(12) United States Patent
Costa et al.

(10) Patent No.: US 10,518,315 B2
(45) Date of Patent: Dec. 31, 2019

(54) APPARATUS AND METHOD FOR FORMING A WAVE FORM FOR A STENT FROM A WIRE

(71) Applicant: Medtronic Vascular, Inc., Santa Rosa, CA (US)

(72) Inventors: Michael Costa, Santa Rosa, CA (US); Lance Ensign, Santa Rosa, CA (US); Dustin Thompson, Santa Rosa, CA (US); Paul Coates, Corte Madera, CA (US); Rui Lam, Santa Rosa, CA (US); Larry Childs, Cotati, CA (US); Justin Eckhardt, Auburn, CA (US); Jerry Warmerdam, Nevada City, CA (US); Charlie Dawson, Chico, CA (US); Bob Boldig, Port Washington, WI (US)

(73) Assignee: Medtronic Vascular, Inc., Santa Rosa, CA (US)

(*) Notice: Subject to any disclaimer, the term of this patent is extended or adjusted under 35 U.S.C. 154(b) by 469 days.

(21) Appl. No.: 15/050,687

(22) Filed: Feb. 23, 2016

(65) Prior Publication Data
US 2016/0167105 A1    Jun. 16, 2016

Related U.S. Application Data

(62) Division of application No. 13/191,134, filed on Jul. 26, 2011, now Pat. No. 9,296,034.

(51) Int. Cl.
*B21F 1/04* (2006.01)
*B21D 7/024* (2006.01)
(Continued)

(52) U.S. Cl.
CPC .............. *B21F 1/04* (2013.01); *A61F 2/82* (2013.01); *B21D 7/02* (2013.01); *B21D 7/024* (2013.01);
(Continued)

(58) Field of Classification Search
CPC ........ B21F 1/04; B21F 23/002; B21F 45/008; B21F 35/04; B21F 9/02; B21F 9/002;
(Continued)

(56) References Cited

U.S. PATENT DOCUMENTS

| | | |
|---|---|---|
| 1,808,019 A | 6/1931 | Clausing |
| 2,153,936 A | 4/1939 | Owens et al. |

(Continued)

FOREIGN PATENT DOCUMENTS

| | | |
|---|---|---|
| CN | 85104375 A | 8/1986 |
| CN | 1962115 A | 5/2007 |

(Continued)

*Primary Examiner* — Edward T Tolan
(74) *Attorney, Agent, or Firm* — Medler Ferro Woodhouse & Mills PLLC

(57) ABSTRACT

An apparatus for forming a wave form for a stent from a wire includes a pair of tension wires configured to rotate about an axis. The tension wires and axis are substantially orthogonal to the stent wire disposed in a gap between the tension wires. When the tension wires are rotated, a bend is formed in the portion of the stent wire disposed between the tension wires. The tension wires may be controlled such that the axis of rotation is aligned with the particular tension wire around which the stent wire is to be bent for each particular bend formed in the stent wire, thereby preventing the particular tension wire from translating during rotation such that the tension wire behaves like a rotary pipe bending die around which the stent wire is bent. A feed assembly feeds the stent wire into the forming area between the tension wires.

20 Claims, 25 Drawing Sheets

(51) Int. Cl.
- *B21D 7/02* (2006.01)
- *B21F 45/00* (2006.01)
- *A61F 2/82* (2013.01)
- B21D 11/07 (2006.01)
- A61F 2/88 (2006.01)

(52) U.S. Cl.
CPC ............ *B21F 45/008* (2013.01); *A61F 2/88* (2013.01); *A61F 2240/001* (2013.01); *B21D 11/07* (2013.01)

(58) Field of Classification Search
CPC ......... B21D 7/02; B21D 7/022; B21D 7/024; B21D 7/04; B21D 11/06; B21D 11/07; A61F 2240/001
See application file for complete search history.

(56) References Cited

U.S. PATENT DOCUMENTS

| | | | |
|---|---|---|---|
| 2,582,576 A * | 1/1952 | Zweyer | B21F 35/04 140/90 |
| 2,590,628 A | 3/1952 | Lessmann | |
| 2,956,608 A | 10/1960 | Vinkemulder | |
| 3,185,185 A | 5/1965 | Pfund | |
| 3,538,736 A | 11/1970 | Nygren | |
| 3,565,129 A | 2/1971 | Field | |
| 3,691,807 A | 9/1972 | Lane et al. | |
| 3,901,064 A * | 8/1975 | Jacobson | B21D 7/022 72/219 |
| 4,043,165 A | 8/1977 | Badger et al. | |
| 4,047,544 A | 9/1977 | Seaborn et al. | |
| 4,079,611 A | 3/1978 | Osterkom et al. | |
| 4,327,570 A | 5/1982 | Schottker | |
| 4,798,073 A | 1/1989 | Dischler | |
| 4,886,062 A | 12/1989 | Wiktor | |
| 4,910,984 A | 3/1990 | Young et al. | |
| 5,019,090 A | 5/1991 | Pinchuk | |
| 5,092,877 A | 3/1992 | Pinchuk | |
| 5,133,732 A | 7/1992 | Wiktor | |
| 5,195,348 A * | 3/1993 | Del Fabro | B21D 11/12 72/217 |
| 5,226,913 A | 7/1993 | Pinchuk | |
| 5,247,823 A | 9/1993 | Rossi | |
| 5,304,200 A | 4/1994 | Spaulding | |
| 5,314,472 A | 5/1994 | Fontaine | |
| 5,324,472 A | 6/1994 | Page et al. | |
| 5,370,683 A | 12/1994 | Fontaine | |
| 5,443,498 A | 8/1995 | Fontaine | |
| 5,527,354 A | 6/1996 | Fontaine et al. | |
| 5,537,852 A * | 7/1996 | Del Fabro | B21D 11/12 72/217 |
| 5,549,663 A | 8/1996 | Cottone, Jr. | |
| 5,653,727 A | 8/1997 | Wiktor | |
| 5,669,261 A | 9/1997 | Castren | |
| 5,694,803 A | 12/1997 | Ervin et al. | |
| 5,716,396 A | 2/1998 | Williams, Jr. | |
| 5,895,406 A | 4/1999 | Gray et al. | |
| 5,902,266 A | 5/1999 | Leone et al. | |
| 5,913,897 A | 6/1999 | Corso, Jr. et al. | |
| 6,042,597 A | 3/2000 | Kveen et al. | |
| 6,117,165 A | 9/2000 | Becker | |
| 6,134,932 A * | 10/2000 | Marque | B21D 7/024 72/149 |
| 6,136,023 A | 10/2000 | Boyle | |
| 6,190,406 B1 | 2/2001 | Duerig et al. | |
| 6,203,569 B1 | 3/2001 | Wijay | |
| 6,308,551 B1 | 10/2001 | Park | |
| 6,342,067 B1 | 1/2002 | Mathis et al. | |
| 6,355,059 B1 | 3/2002 | Richter et al. | |
| 6,423,091 B1 | 7/2002 | Hojeibane | |
| 6,432,132 B1 | 8/2002 | Cottone et al. | |
| 6,447,540 B1 | 9/2002 | Fontaine et al. | |
| 6,503,270 B1 | 1/2003 | Richter et al. | |
| 6,568,432 B2 | 5/2003 | Matsutani et al. | |
| 6,610,086 B1 | 8/2003 | Kock et al. | |
| 6,656,219 B1 | 12/2003 | Wiktor | |
| 6,730,117 B1 | 5/2004 | Tseng et al. | |
| 6,736,844 B1 | 5/2004 | Glatt et al. | |
| 6,878,162 B2 | 4/2005 | Bales et al. | |
| 6,923,828 B1 | 8/2005 | Wiktor | |
| 6,969,402 B2 | 11/2005 | Bales et al. | |
| 7,004,968 B2 | 2/2006 | Lootz et al. | |
| 7,108,714 B1 | 9/2006 | Becker | |
| 7,169,175 B2 | 1/2007 | Cottone, Jr. et al. | |
| 7,329,277 B2 | 2/2008 | Addonizio et al. | |
| 2002/0095208 A1 | 7/2002 | Gregorich et al. | |
| 2003/0010084 A1 * | 1/2003 | Latour | B21D 7/022 72/307 |
| 2003/0083736 A1 | 5/2003 | Brown et al. | |
| 2004/0044401 A1 | 3/2004 | Bales et al. | |
| 2004/0143318 A1 | 7/2004 | Tseng et al. | |
| 2005/0268688 A1 * | 12/2005 | Chien | B21D 11/12 72/387 |
| 2006/0030934 A1 | 2/2006 | Hogendijk et al. | |
| 2006/0079955 A1 | 4/2006 | Brown | |
| 2008/0097580 A1 | 4/2008 | Dave | |
| 2008/0097582 A1 | 4/2008 | Shanley et al. | |
| 2008/0183273 A1 | 7/2008 | Mesana et al. | |
| 2008/0288053 A1 | 11/2008 | Addonizio et al. | |
| 2008/0289389 A1 | 11/2008 | Fitch et al. | |
| 2008/0294241 A1 | 11/2008 | Addonizio et al. | |
| 2008/0306583 A1 | 12/2008 | Bashiri et al. | |
| 2008/0319529 A1 | 12/2008 | Krivoruchko et al. | |
| 2008/0319534 A1 | 12/2008 | Birdsall et al. | |
| 2008/0319535 A1 | 12/2008 | Craven et al. | |
| 2009/0005848 A1 | 1/2009 | Strauss et al. | |
| 2009/0024207 A1 | 1/2009 | Addonizio et al. | |
| 2009/0036976 A1 | 2/2009 | Beach et al. | |
| 2009/0260411 A1 * | 10/2009 | Knewtson | B21F 1/04 72/387 |
| 2010/0161035 A1 | 6/2010 | Shehata | |
| 2010/0269950 A1 | 10/2010 | Hoff et al. | |

FOREIGN PATENT DOCUMENTS

| | | | |
|---|---|---|---|
| CN | 101925370 A | 12/2010 | |
| EP | 0565251 A1 | 10/1993 | |
| EP | 945107 | 9/1999 | |
| EP | 1155664 | 11/2007 | |
| EP | 1932603 A1 | 6/2008 | |
| FR | 2793673 A1 | 11/2000 | |
| GB | 873646 A * | 7/1961 | ............... B21D 7/02 |
| GB | 2085776 | 5/1982 | |
| GB | 2281865 | 3/1995 | |
| JP | 58-16735 A * | 1/1983 | ............. B21D 7/024 |
| WO | WO2007/080611 | 7/2007 | |
| WO | WO2007/095466 | 8/2007 | |
| WO | WO2007/133039 | 11/2007 | |
| WO | WO2008/028964 | 3/2008 | |
| WO | WO2008/049045 | 4/2008 | |
| WO | WO2008/100783 | 8/2008 | |
| WO | WO2009/128983 | 10/2009 | |
| WO | WO2011/034793 | 3/2011 | |

\* cited by examiner

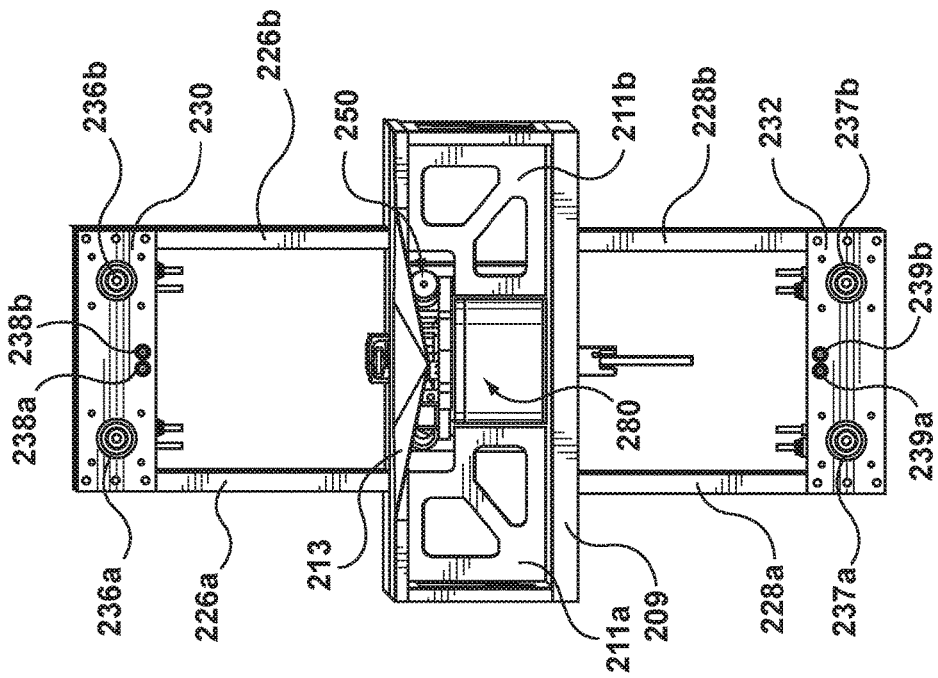
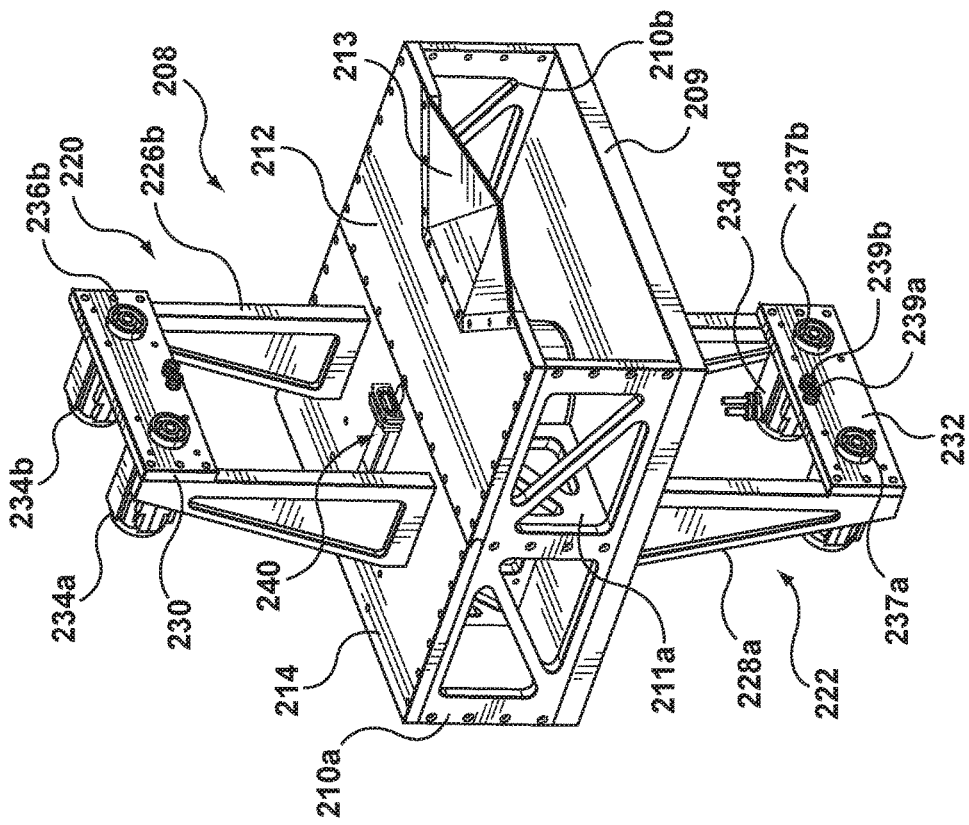

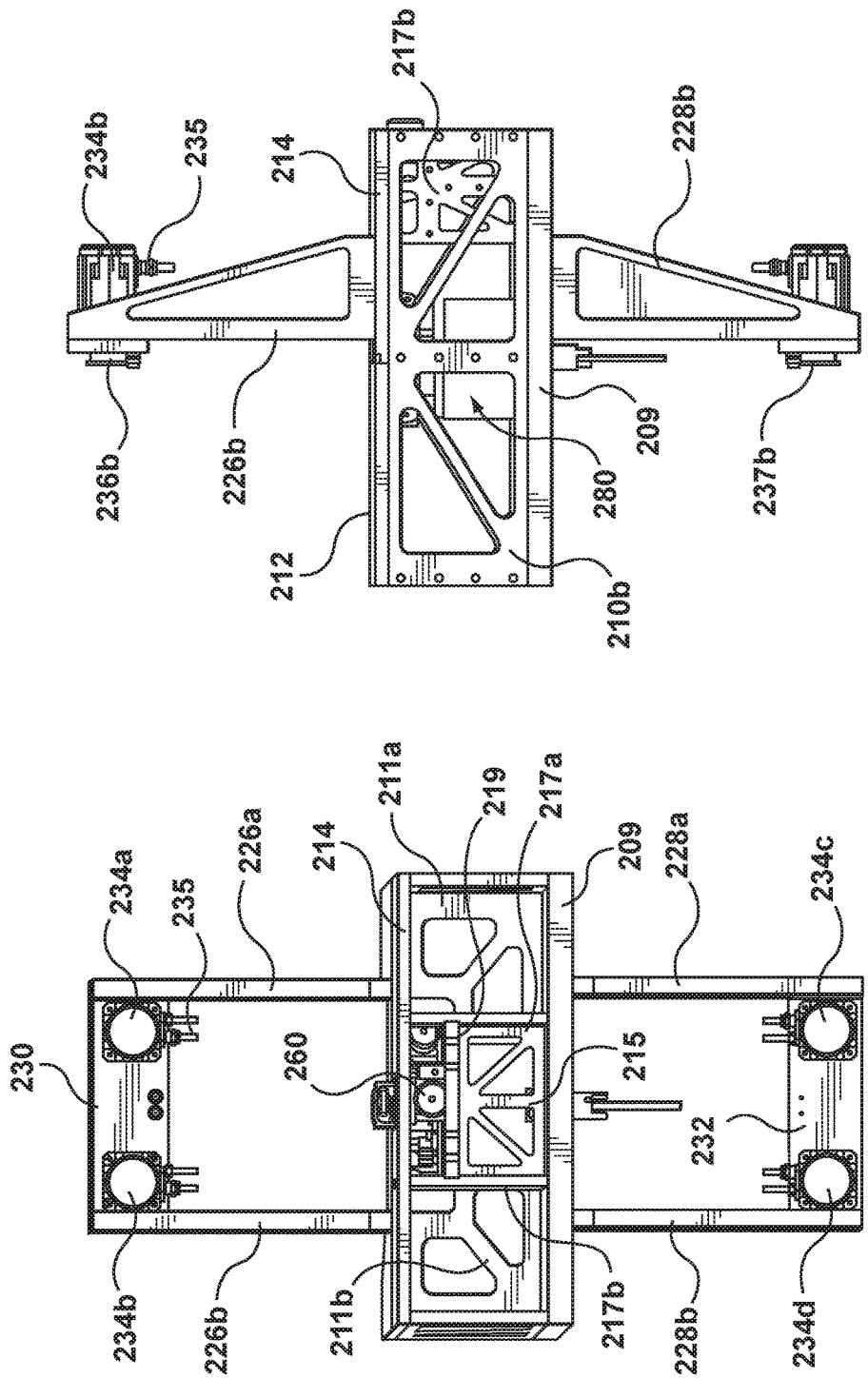

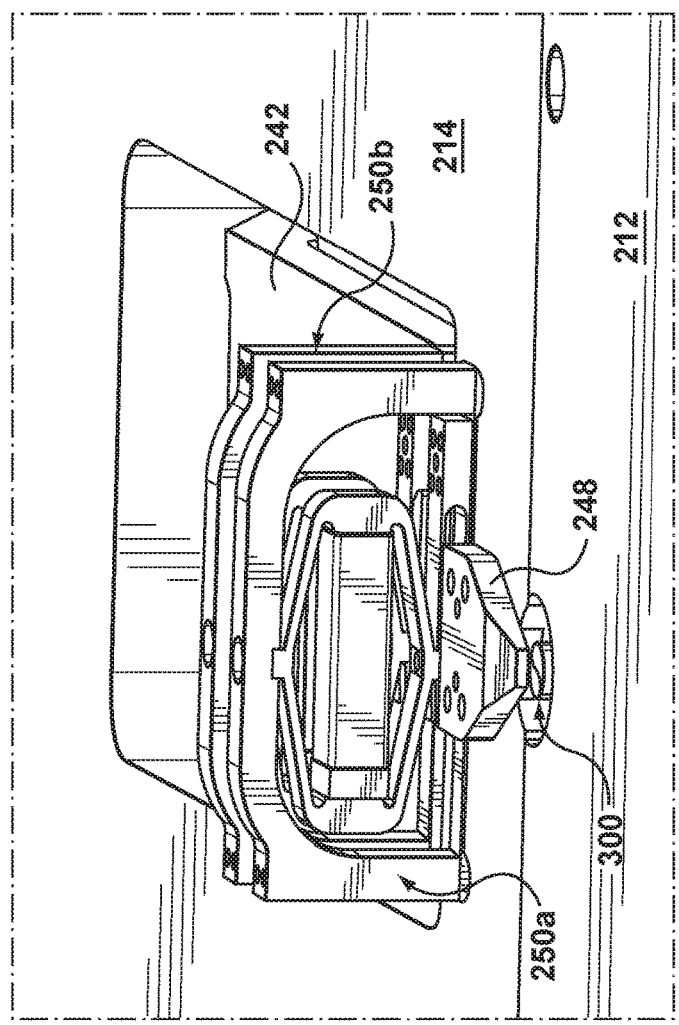

APPARATUS AND METHOD FOR FORMING A WAVE FORM FOR A STENT FROM A WIRE

RELATED APPLICATIONS

This application is a Division of and claims the benefit of U.S. patent application Ser. No. 13/191,134 filed Jul. 26, 20111, now allowed. The disclosures of which are herein incorporated by reference in their entirety.

BACKGROUND OF THE INVENTION

Field of the Invention

The present invention is generally related to an apparatus and method for forming a wave form for a stent. More particularly, the present invention is related to an apparatus and method for forming the wave form from a wire.

Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s), may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped around the longitudinal axis at a non-perpendicular angle.

A stent that includes a helical coil may be formed from a single wire that includes a wave form that is configured to allow the stent to radially expand. In view of the small size of the stents, it may be difficult to form a stent from a single wire while controlling the wave form so that individual waves may vary in size and shape. Further, accurately and uniformly bending the stent wire without adversely deforming the stent wire is difficult. Accordingly, there is a need for apparatus and methods for accurately and uniformly forming a wave form in a stent wire such that each wave of the wave form can be individually controlled for size and shape.

SUMMARY OF THE INVENTION

Embodiments of the present invention describe apparatus and methods for forming a wave form for a stent from a single wire.

According to an embodiment, there is provided an apparatus and method for forming a wave form for a stent from a wire. The apparatus includes a pair of tension wires disposed substantially parallel to each other with a gap disposed therebetween. The tension wires are in tension and are coupled to a device such that the tension wires rotate relative to a rotation axis. A portion of a stent wire is disposed in the gap between the tension wires such that the stent wire is substantially perpendicular to the tension wires. Rotation of the tension wires with the stent wire disposed therebetween causes the tension wires to bend the stent wire, thus forming a crown therein. The tension wires are rotated back to a neutral position and a length of the stent wire is fed between the tension wires. The tension wires are rotated in the opposite direction to bend the stent wire to create a second crown disposed in a direction opposite the first crown. The tension wires are rotated back to the neutral position and a length of stent wire is fed between the tension wires. This process is repeated to create a wave form wherein each wave of the wave form can be controlled for amplitude, shape, and wave length by controlling the length of stent wire fed and the amount of rotation of the tension wires.

According to an embodiment, there is provided an apparatus and method for forming a wave form for a stent from a wire. The apparatus includes a pair of tension wires disposed substantially parallel to each other with a gap disposed therebetween. The tension wires are in tension and each tension wire is coupled to a wire holder that can be rotated and translated. The translation of the individual wire holders allows the axis of rotation to be aligned with the tension wire around which the stent wire is to be bent. The translation of the individual wire holders also allows the gap between the tension wires to be dynamically adjusted such that the tension wires are abutting the stent wire during bending of the stent wire and such that the gap is larger when the wire holders are returned to a neutral position and when the stent wire is fed between the tension wires. A portion of a stent wire is disposed in the gap between the tension wires such that the stent wire is substantially perpendicular to the tension wires. The wire holders are translated such that the first tension wire around which the stent wire is to be bent is aligned with the axis of rotation and the tension wires abut the stent wire. The wire holders are rotated in a first direction to bend the stent wire to form a crown in the stent wire. The wire holders are separated, returned to the neutral position, and a length of stent wire is fed between the tension wires. The wire holders are translated such that the second tension wire around which the stent wire is to be bent is aligned with the axis of rotation and the tension wires abut the stent wire. The wire holders are rotated in a second direction opposite the first direction to bend the stent wire to form a second crown in a direction opposite the first crown, thereby completing a wave of the wave form. The wire holders are separated, returned to the neutral position, and a length of the stent wire is fed between the tension wires. This process is repeated to create a wave form wherein each wave of the wave form can be controlled for amplitude, shape, and wave length by controlling the length of stent wire fed and the amount of rotation of the tension wires.

According to an embodiment, there is provided an apparatus and method for forming a wave form for a stent from a wire. The apparatus includes elongated forming members with rounded ends to bend the stent wire. The forming members are independently controlled and can be translated and rotated. In an embodiment, the forming members are mounted to a respective drum or cylinder which is independently translatable and rotatable to thereby translate and rotate the respective forming member attached thereto. A stent wire is disposed between the forming members and the forming members are translated and rotated relative to each other to form bends in the stent wire and/or feed additional lengths of the stent wire into the forming area. The elongated, rounded, relatively stiff forming members bend the stent wire with minimal or no deformation of the stent wire, particularly in the stent wire cross-section.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 24 is a perspective view of the apparatus of FIG. 24 with some support structure removed.

FIG. 25 is a front view of the apparatus of FIG. 24.

FIG. 26 is a rear view of the apparatus of FIG. 24.

FIG. 27 is a side view of the apparatus of FIG. 24.

FIGS. 37A and 37B are perspective views of the feed assembly of FIG. 36 with an upper guide plate removed and included, respectively.

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
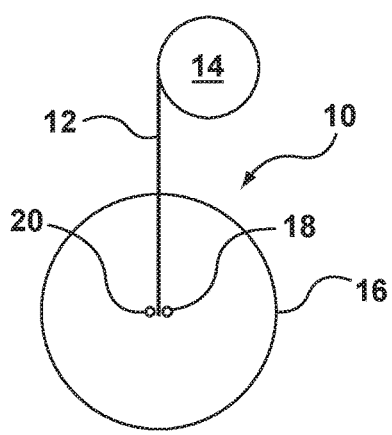
FIGS. 1-8 are schematic views of an embodiment of an apparatus and a method for forming a wave form for a stent from a wire.

FIG. 1 schematically illustrates a portion of an apparatus 10 for forming a wave form for a stent from a stent wire 12. A supply 14 of the wire 12 is provided to the apparatus 10. In an embodiment, the supply 14 may include a spool upon which the wire 12 is wound. Tension wires 18 and 20 are attached at one end to a plate 16. Tension wires 18 and 20 are also fixed at an end opposite plate 16 such that tension wires 18, 20 are in tension and are generally perpendicular/orthogonal to wire 12. Tension wires 18, 20 are spaced apart from each other such that wire 12 may be disposed between tension wires 18, 20, as will be described in more detail below. As would be understood by those of ordinary skill in the art, supply 14 may be any device or method for providing a supply of wire 12 and feeding or pushing the wire 12 through the space between tension wires 18, 20. Wire 12 may have any suitable diameter for the intended stent application. For example, and not by way of limitation, wire 12 may have a diameter between about 0.0025 inch and about 0.0075 inch. Wire 12 may be formed of any material suitable for the intended application. For example, and not by way of limitation, wire 12 may be formed from stainless steel, nickel-titanium alloys (Nitinol™), cobalt-chromium alloys (e.g. L605, MP35N), composite wire (e.g. MP35N sheel with tantalum core wire), precious metal alloys, nickel based super-alloys, magnesium based alloys, zinc based alloys, and various polymers. Similarly, tension wires 18, 20 may be made of any suitable material and have any suitable diameter to bend wire 12, as described in detail below, and provide adequate durability in the process for bending wire 12. For example, and not by way of limitation, in one embodiment, tension wires 18, 20 are made from a nickel-titanium alloy (Nitinol™) and have a diameter of in the range of about 0.003 inch to about 0.010 inch.

Plate 16 is shown circular in the drawings. However, plate 16 may be any suitable shape to perform the function of holding tension wires 18, 20 in tension, and rotating such that tension wires 18, 20 bend wire 12, as described in more detail below. In the embodiment shown, one end of each of the tension wires 18, 20 is attached to the plate 16 and the opposite end of each of the tension wires 18, 20 is attached to a device to keep the tension wires 18, 20 in tension. For example, and not by way of limitation, the tension device may be a weight or a tension motor. An embodiment using a tension motor is described in more detail below.

Figure 2:
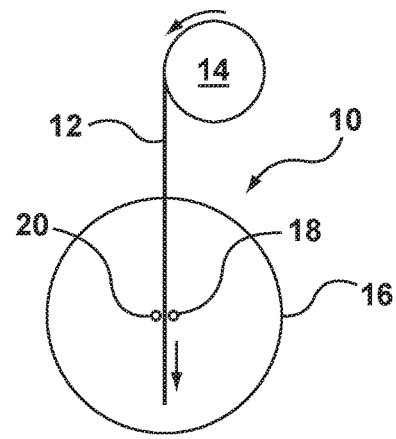
Figure 3:
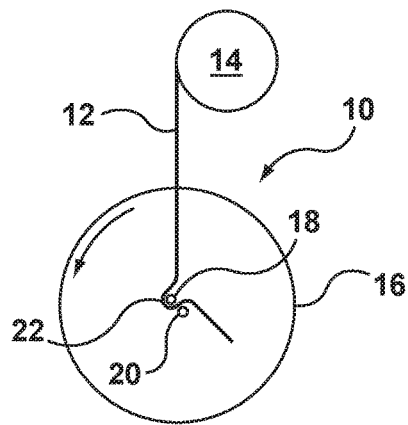

Supply 14 pushes wire 12 through the space between tension wires 18, 20, as shown in FIG. 2. Supply 14 may be controlled by a controller such that the length of wire 12 pushed between tension wires 18, 20 is controlled. Next, plate 16, with tension wires 18, 20 attached thereto, rotates in a direction such that tension wires 18, 20 also rotate, as shown in FIG. 3. In one embodiment shown in FIG. 3, plate 16 rotates counter-clockwise, as indicated by the arrow in FIG. 3. As plate 16 and tension wires 18, 20 rotate, tension wires 18, 20 bend the portion of wire 12 that is disposed in the space between tension wires 18, 20. The amount of rotation of plate 16 controls the amount of bend on wire 12. For example, and not by way of limitation, plate 16 may rotate between 90 and 180 degrees to bend wire 12 to create a first crown 22 in wire 12.

Figure 4:
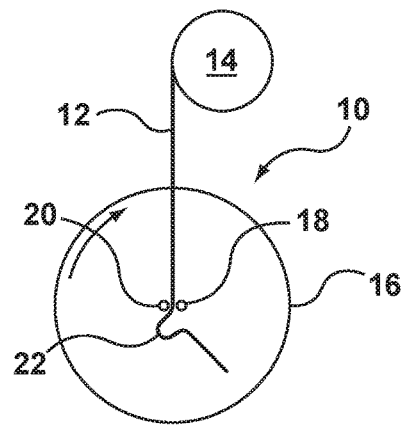
Figure 5:
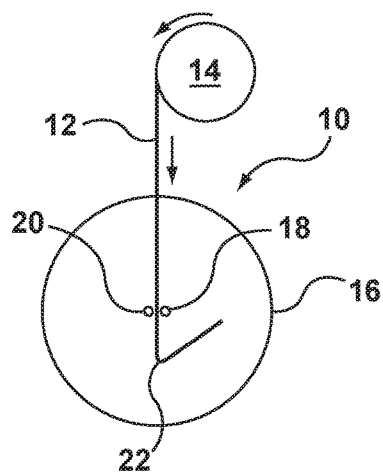
Figure 6:
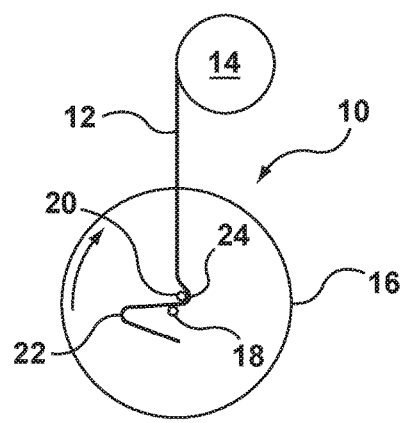
Figure 7:
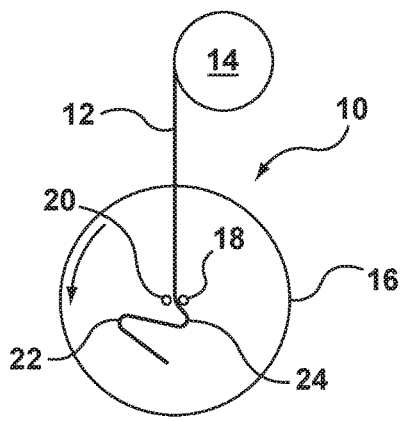

Next, plate 16 is rotated in a clockwise direction back to the neutral position, as shown in FIG. 4. There is sufficient space between tension wires 18, 20 such that wire 12 is not bent by the return of plate 16 back to the neutral position. Supply 14 then pushes wire 12 the desired length of the amplitude of the waveform, as shown in FIG. 5. Plate 16 then rotates in a clockwise direction, as shown in FIG. 6, such that tension wires 18, 20 rotate with wire 12 disposed therebetween. As plate 16 and tension wires 18, 20 rotate, tension wires 18, 20 bend the portion of wire 12 disposed in the space between tension wires 18, 20. Due to rotation of plate 16 in the opposite direction of the previous rotation, a second crown 24 is formed in wire 12 in the opposite direction of the first crown 22, thereby completing a wave of the waveform. Next, plate 16 is returned to the neutral position by rotating plate 16 back in the counter-clockwise direction, as shown in FIG. 7.

Figure 8:
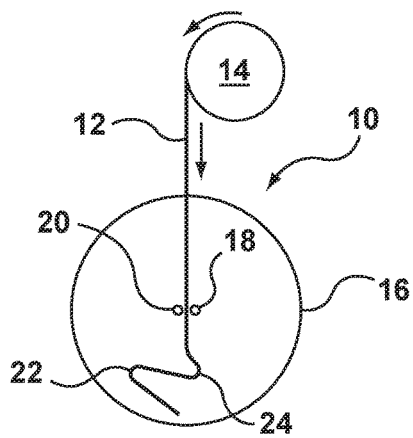
Figure 9:
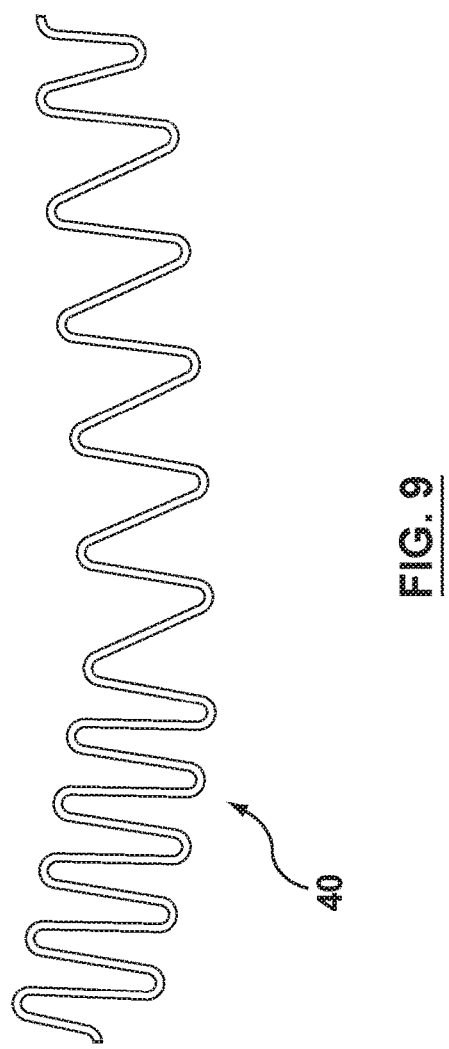
FIG. 9 is a schematic view of a waveform that may be produced with the apparatus and method of FIGS. 1-8.

Another desired length of wire 12 may then be advanced between tension wires 18, 20, as shown in FIG. 8, and the above described steps may be repeated as many times as desired to create the desired wave form 40. For example, FIG. 9 illustrates an embodiment of a wave form 40 that may be produced by apparatus 10 utilizing the method described above. Of course, many other shapes may be formed and the embodiment illustrated in FIG. 9 is not intended to be limiting in any way. In particular, a controller coupled to supply 14 and the motor (not shown) used to rotate plate 16 may control each feed of wire 12 and each rotation of plate 16. Thus, each wave that is formed may be different, i.e., may have a different amplitude, wavelength, shape, etc., as compared to adjacent waves. In an embodiment, each wave of the wave form may have a unique amplitude and wavelength.

FIGS. 10-21 illustrate schematically a portion of an apparatus 100 for forming a wave form for a stent from a stent wire 112 in accordance with another embodiment herein. Like the embodiment illustrated in FIGS. 1-8, wire 112 is provided to the apparatus 100 by a supply 114, which may include a spool upon which the wire 112 is wound. Rather than a single plate 16 described in FIGS. 1-8, apparatus 100 includes a first die or wire holder 116 and a second die or wire holder 117. Wire holders 116, 117 are disposed adjacent to each other along parting lines 128, 126 respectively. In the embodiment shown, parting lines 128, 126 are curved. In this manner, stent wire 112 is prevented from sliding between wire holders 116, 117 during the forming process, described in more detail below. Stent wire 112 is supported by a portion of wire holder 116 or a portion of wire holder 117 throughout the wave forming process. Each wire holder 116, 117 includes a recess or groove 130, 132 sized to retain a corresponding tension wire 118, 120 therein. Tension wires 118, 120 may be the same as tension wires 18, 20 described above. Tension wires 118, 120 extend generally perpendicular/orthogonal to stent wire 112 such that stent wire 112 is disposed between tension wires 118, 120. For example, and not by way of limitation, tension wires 118, 120 may extend generally vertically and stent wire 112 may extend generally horizontally.

In the particular embodiment shown, tension wires 118, 120 extend through wire holders 116, 117, as will be described in more detail below. Tension wires 118, 120 are held in tension by means known to those skilled in the art. For example, and not by may of limitation, corresponding ends of tension wires 118, 120 may be secured and a weight or motor coupled thereto to provide a tensile force. An embodiment of a tension motor driver is described in more detail below and can be used with any of the embodiments described herein. However, other apparatus and methods for providing a tensile force to tension wires 118, 120 may be utilized.

Figure 10:
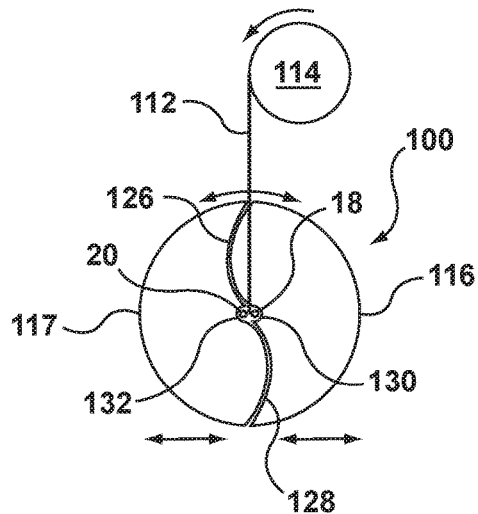
FIGS. 10-21 are schematic views of an embodiment of an apparatus and a method for forming a wave form for a stent from a wire.

As indicated by the arrows in FIG. 10, wire holders 116, 117 may translate laterally and rotate. Although the arrows in FIG. 10 show wire holders 116, 117 translating generally perpendicular to the direction of the stent wire, wire holders 116, 117 may translate at any position along its rotation. Thus, for example, and not by way of limitation, if wire holders 116, 117 are rotated approximately 90 degrees, translation of the wire holders 116, 117 would be generally parallel to the stent wire 112.

Figure 11:
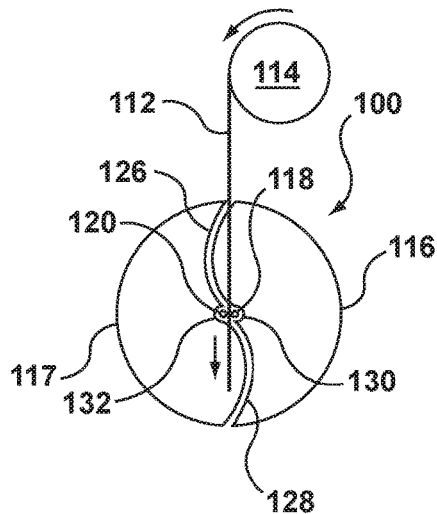
Figure 12:
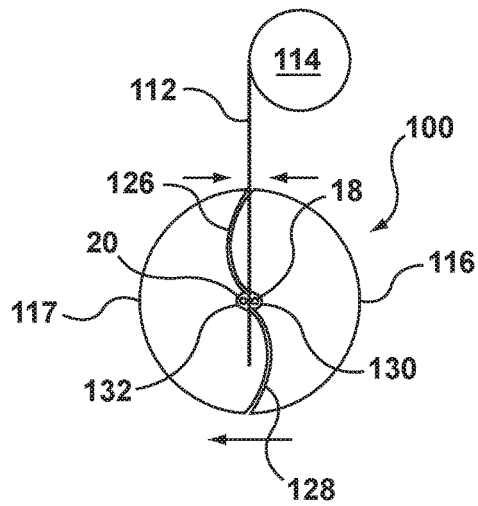
Figure 22:
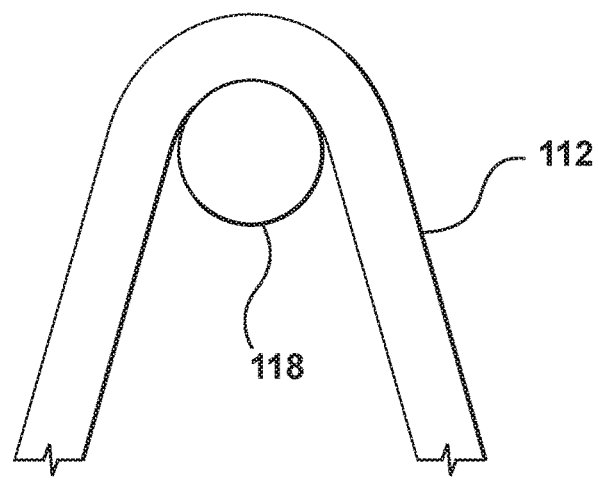
FIG. 22 is a schematic close-up view of a stent wire bent around a tension wire to form a crown.

In an embodiment of a method of forming a waveform in stent wire 112, wire holders 116, 117 are moved apart from each other and supply 114 feeds a length of stent wire 112 between tension wires 118, 120, as shown in FIG. 11. Next, wire holders 116, 117 are moved towards each other such that tension wires 118, 120 are closely adjacent to/abutting stent wire 112. Further, wire holders 116, 117 are shifted to the left such that the right tension wire 118 is aligned with the center of rotation of the wire holder 116, 117, as shown in FIG. 12. By aligning the right tension wire 118 with the center of rotation, right tension wire 118 does not translate during rotation, behaving like a rotary pipe bending die around which stent wire 112 is bent, as shown in FIG. 22.

Figure 13:
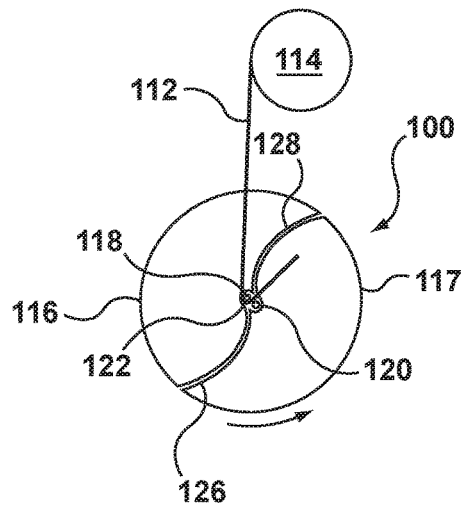

Next the wire holders 116, 117 are rotated in a counter-clockwise direction, as shown in FIG. 13. This rotation causes the left tension wire 120 to rotate around the right tension wire 118 if the right tension wire is located at the center of rotation. Such a rotation causes the stent wire 112 disposed between tension wires 118, 120 to bend, as shown in FIG. 13, thereby forming a first crown 122 in the stent wire 112.

Figure 14:
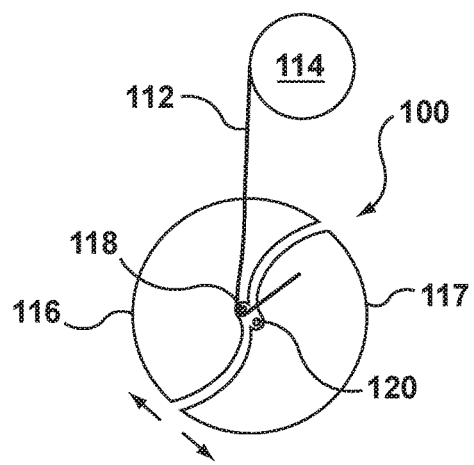
Figure 15:
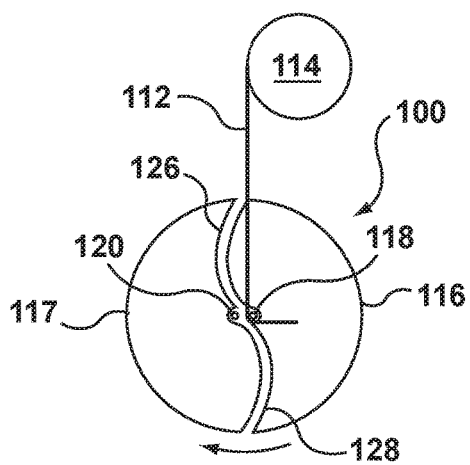
Figure 16:
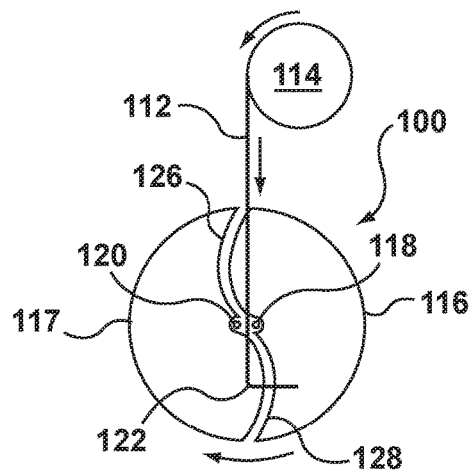

The wire holders 116, 117 are then translated to separate from each other such that the gap between the tension wires 118, 120 is increased, as shown in FIG. 14. This permits the wire holders 116, 117 to return to the neutral position through a clockwise rotation of wire holders 116, 117, as shown in FIG. 15, without bending stent wire 112. With wire holders 116, 117 still separated, another length of stent wire 112 is fed from supply 114, as shown in FIG. 16.

Figure 17:
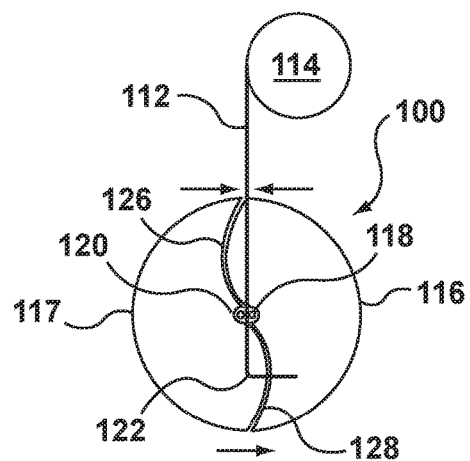
Figure 18:
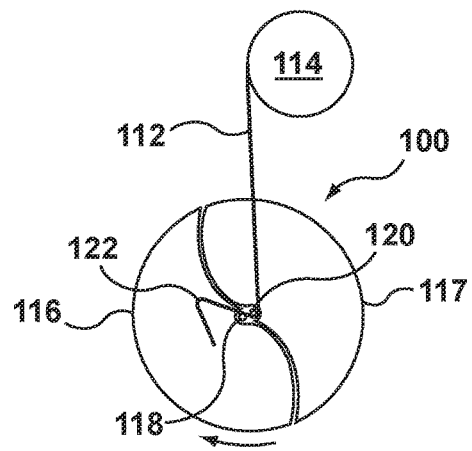

Next, the wire holders 116, 117 are translated towards each other and shifted to the right such that tension wires 118, 120 are closely adjacent to/abutting stent wire 112 and left tension wire 120 is disposed at the center of rotation of the wire holders 116, 117, as illustrated in FIG. 17. Wire holders 116, 117 are then rotated in a clockwise direction, as shown in FIG. 18. This rotation causes the right tension wire 118 to rotate around the left tension wire 120 if the left tension wire 120 is located at the center of rotation. Such a rotation causes the stent wire 112 disposed between tension wires 118, 120 to bend as if in a rotary type pipe bender, as shown in FIG. 18, thereby forming a second crown 124 in the stent wire 112 and completing a wave of the waveform.

Figure 19:
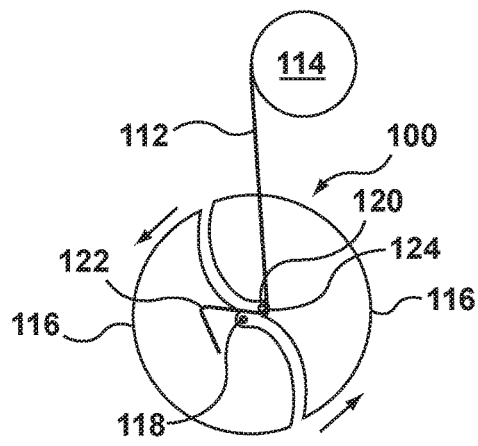
Figure 20:
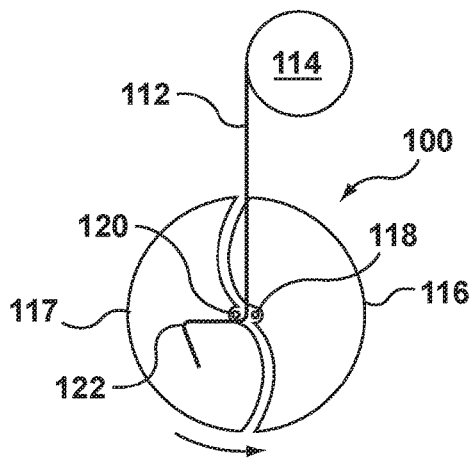
Figure 21:
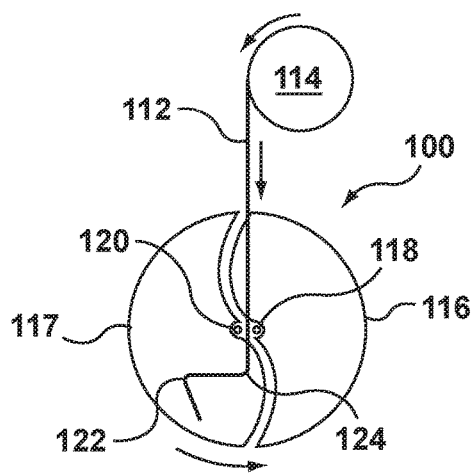

The wire holders 116, 117 are then translated to separate from each other such that the gap between the tension wires 118, 120 is increased, as shown in FIG. 19. This permits the wire holders 116, 117 to return to the neutral position through a counter-clockwise rotation of wire holders 116, 117, as shown in FIG. 20, without bending stent wire 112. With wire holders 116, 117 still separated, another length of stent wire 112 is fed from supply 114, as shown in FIG. 21. The above-described steps may then be repeated as many times as desired to complete the desired waveform. The size and shape of each individual wave may be controlled by controlling the length of stent wire 112 fed from supply 114 and the amount of rotation of wire holders 116, 117. Thus, a waveform with varying wave lengths, amplitudes, and degree of bend in the crowns may be created from a single stent wire.

FIGS. 23-39 show an embodiment of an apparatus 200 for forming a waveform in a stent wire. Apparatus 200 utilizes the principles discussed above with respect to apparatus 100 in that a pair of wire holders are used that can translate and rotate and are utilized to hold tension wires that form crowns in the stent wire. The description of apparatus 200 includes many details of specific embodiments for operating the wire holders, tension wires, and feeding the stent wire. Those skilled in the art would recognize that the various features described with respect to apparatus 200 can be used, individually or in combination, as appropriate in the other embodiments described herein.

Figure 23:
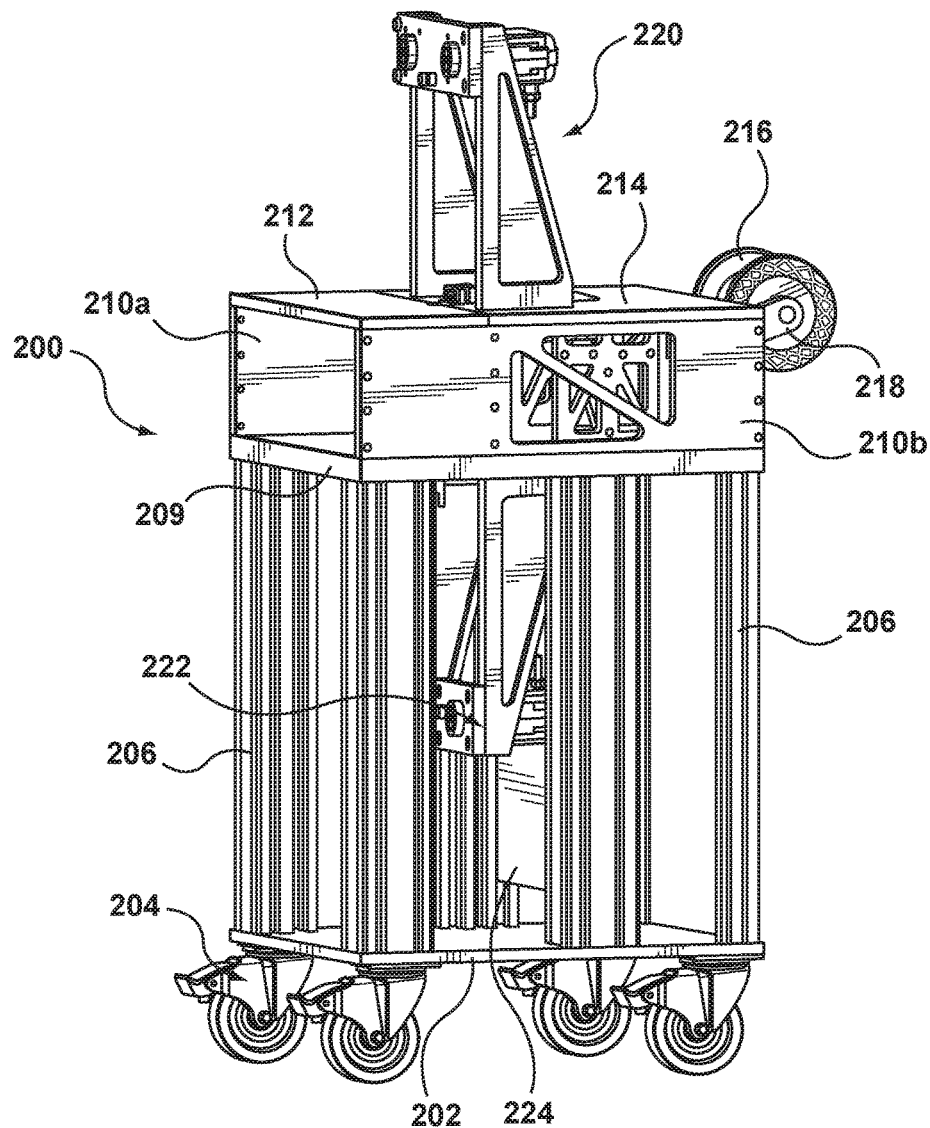
FIG. 23 is a perspective view of an embodiment of an apparatus for forming a wave form for a stent from a wire.

FIG. 23 is a perspective view of apparatus 200. Apparatus 200 includes a base plate 209, and stand base 202, and legs 206 attached at each end to the base plate 209 and stand base 202. Further, brake wheels 204 are attached to the stand base. The base plate 209, stand base 202, and legs 206 provide support for the base plate assembly 208 (FIG. 24), which includes many of the elements for forming a waveform in a stent wire. Apparatus 200 further includes an electronics panel 224, which houses a power supply, servo drives, and other electronics known to those of ordinary skill in the art that are needed or desired for the parts described herein.

As illustrated in FIGS. 23-27, left and right upper shelf side supports 210a, 210b are attached to base plate 209. Left and right upper shelf side supports 210a, 210b support a front upper shelf 212 and a rear upper shelf 214. Front upper shelf 212 includes a guide tray 213 attached thereto. Left and right inner upper shelf supports 211a, 211b extend from the left and right upper shelf side supports 210a, 210b towards the interior of apparatus 200 to further support the upper shelf 212, 214, as illustrated in FIGS. 25 and 26. Disposed in the rear portion of the base assembly 208 between the rear upper shelf 214 and the base plate 209 are a feed axis center support 215, left and right feed axis side supports 217a, 217b, and a feed axis support shelf 219, as illustrated in FIG. 26. These support a feeder assembly 240, described in more detail below.

A spool 216 for holding a supply of the stent wire is attached to the rear upper shelf 214, as shown generally in FIG. 23. In the embodiment shown, as illustrated in more detail in FIG. 29, a bracket 219 is attached to the lower surface of the rear upper shelf 214. A spool arm 218 extends from the bracket 219 to the rear of rear upper shelf 214. A spindle 223 extends from spool arm 218. Spool 216 includes an opening 216a and spindle 223 extends through opening 216a to support spool 216.

An upper tension drive assembly 220 is attached to rear upper shelf 214 and extends upwardly, as shown in FIGS. 23-28. Upper tension drive assembly 220 includes left and right upper tension drive risers 226a, 226b attached to the rear upper shelf 214. An upper tension motor plate 230 is attached to the left and right tension upper drive risers 226a, 226b and spans the gap therebetween. The upper tension motor plate 230 serves as a mounting plate for left and right upper tension motors 234a, 234b. Left and right upper tension motors 234a, 234b are operatively connected to left and right upper pulleys 236a, 236b, respectively. In the embodiment shown in FIGS. 23-28, the left and right upper tension motors 234a, 234b are disposed on a rear side of upper tension motor plate 230, the left and right upper tension pulleys 236a, 236b are disposed on a front side of upper tension motor plate 230, and left and right motor shafts extend through respective openings in the upper tension motor plate 230 to operatively connect the left and right upper tension motors 234a, 234b to the left and right upper tension pulleys 236a, 236b. Upper tension drive assembly further includes left and right upper guide pulleys 238a, 238b, as shown.

Similarly, a lower tension drive assembly 222 is attached to base plate 209 and extends downwardly, as shown in FIGS. 23-28. Lower tension drive assembly 222 includes left and right lower tension drive risers 228a, 228b attached to the base plate 209. A lower tension motor plate 232 is attached to the left and right lower tension drive risers 228a, 228b and spans the gap therebetween. The lower tension motor plate 232 serves as a mounting plate for left and right lower tension motors 234c, 234d. Left and right lower tension motors 234c, 234d are operatively connected to left and right lower pulleys 237a, 237b, respectively. In the embodiment shown in FIGS. 23-28, the left and right lower tension motors 234c, 234d are disposed on a rear side of lower tension motor plate 232, the left and right lower tension pulleys 237a, 237b are disposed on a front side of lower tension motor plate 232, and left and right motor shafts extend through respective openings in the upper tension motor plate 230 to operatively connect the left and right lower tension motors 234c, 234d to the left and right lower tension pulleys 237a, 237b. Lower tension drive assembly further includes left and right lower guide pulleys 239a, 239b, as shown.

Figure 28:
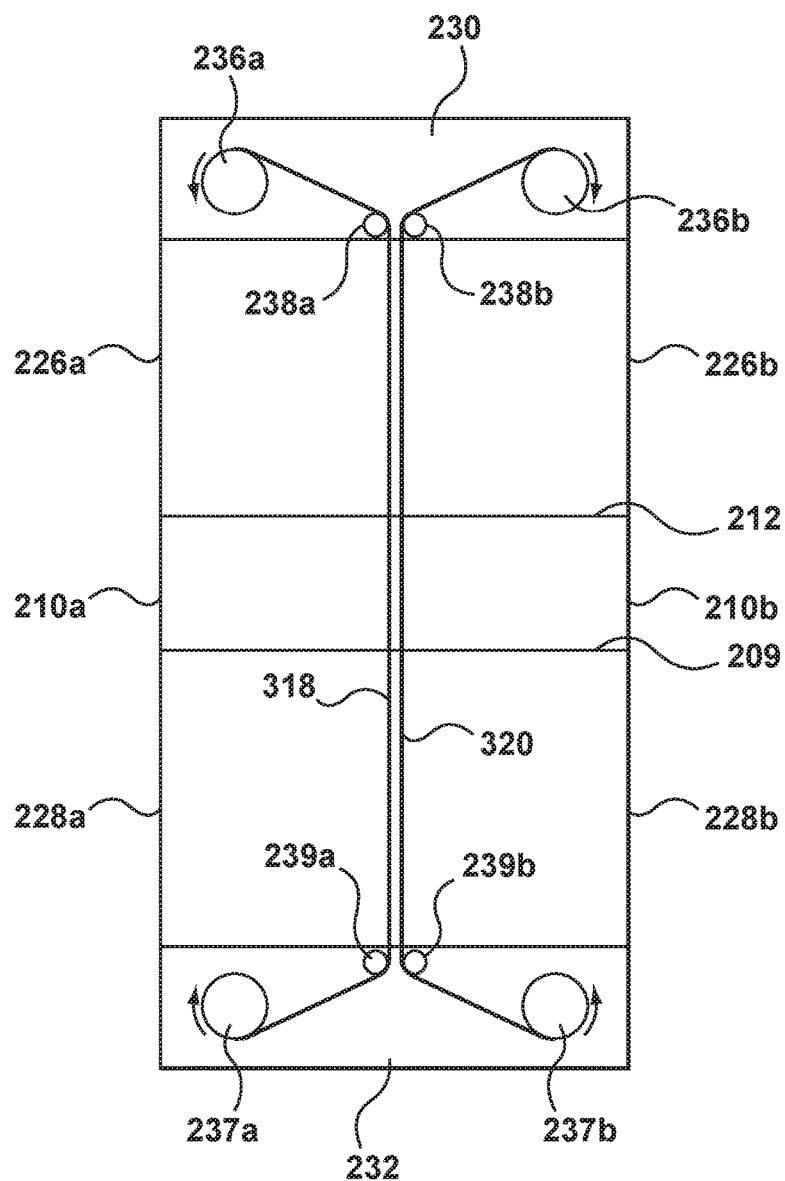
FIG. 28 is a front schematic view of the apparatus of FIG. 24 with tension wires shown.
Figure 29:
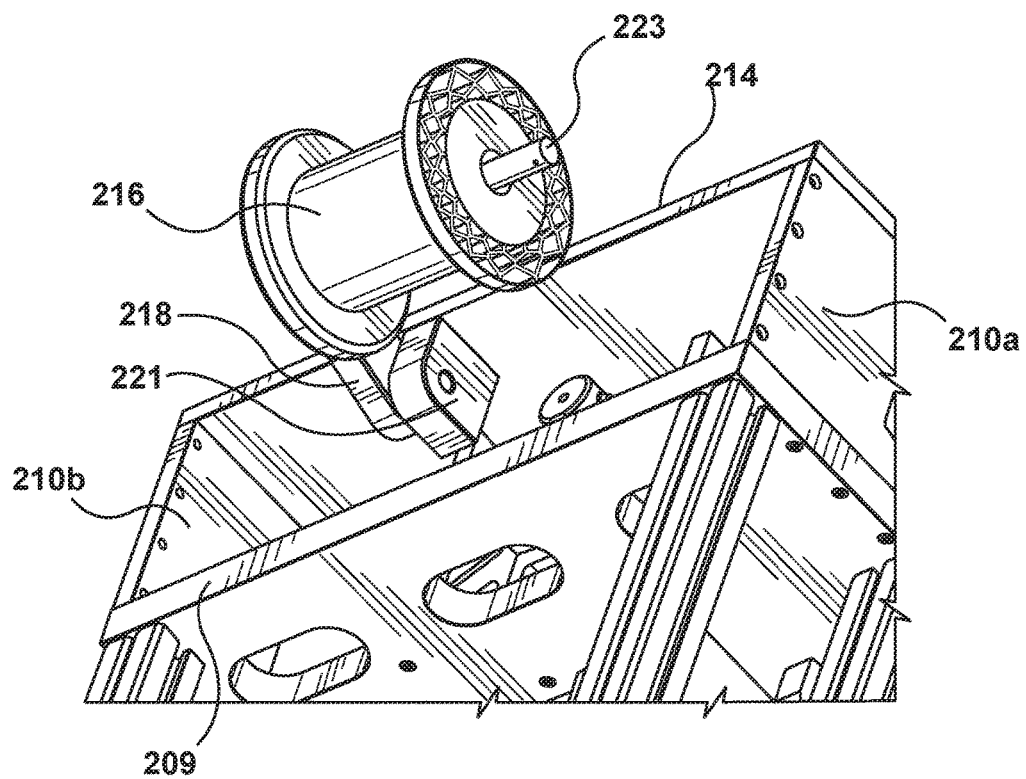
FIG. 29 is a schematic view of the spool area of the apparatus of FIG. 23.

Left and right upper tension motors 234a, 234b and left and right lower tension motors 234c, 234d may be, for example and not by way of limitation, Danaher AKM gear motors, such as the Danaher AKM-21x, or other similar motors. In operation, as illustrated in FIG. 28, left and right tension wires 318, 320 are maintained in tension by the upper and lower tension drive assemblies 220, 222. Left and right tension wires 318, 320 may be similar to tension wires 18, 20 and 118, 120 described with respect to the embodiments above. In the particular embodiment shown, left tension wire 318 is wound around upper left pulley 236a, extends along an inner or right side of left upper guide pulley 238a, and down through the left wire holder (not shown in FIG. 28). The left tension wire 318 continues downward along the inner or right side of left lower guide pulley 239a and is wound around lower left pulley 237a. Similarly, right tension wire 320 is wound around upper right pulley 236b, extends along an inner or left side of right upper guide pulley 238b, and down through the right wire holder (not shown in FIG. 28). The right tension wire 320 continues downward along the inner or left side of right lower guide pulley 239b and is wound around lower left pulley 237b.

In operation, tension motors 234a, 234b, 234c, 234b provide a force to maintain tension wires 318, 320 in tension. In particular, left upper tension motor 234a provides a counter-clockwise force and left lower tension motor 234c provides a clockwise force to maintain left tension wire 318 in tension, as indicated by the arrows in FIG. 28. Right upper tension motor 234b provides a clockwise force and right lower tension motor 234d provides a counter-clockwise for to maintain right tension wire 320 in tension, as also indicated by the arrows in FIG. 28. However, each of the tension motors may also step in the opposite direction in order to move the respective tension wire. For example, upper right tension motor 236b may step in the counter-clockwise direction and lower right tension motor 236d may step the corresponding amount in the clockwise direction such that right tension wire 318 shifts downward. These steps may be as small as to move the corresponding tension wire 0.001 inch. This movement reduces wear on the tension wires 318, 320, which provide longer life for the tension wires and reduces wear marks or variations on the stent wire when the stent wire is bent by the tension wires. In particular, after each crown in the stent wire is formed as described with respect to FIGS. 10-21, each of the tension wires 318, 320 may be shifted up or down such that a "fresh" portion of the tension wires is used for the next crown. For example, and not by way of limitation, if the stent wire is 0.0035 inch in diameter, the tension wires may be shifted by the length of the portions of the tension wires that contact the stent wire during the formation of each crown, e.g. 0.002 inch, after each crown is formed. In forming 1000 crowns, only 2 inches of the tension wires will be utilized, and each crown is formed using an unworn portion of the tension wires. The tension wires 318, 320 may be spooled around the respective pulleys 236a, 237a, 236b, 237b such that tens of thousands of crowns may be formed without using the same portion of the tension wires 318, 320 more than once. When the tension wires 318, 320 have moved to their limit in one direction, the tension wires 318, 320 can be shifted incrementally in the opposite direction to form tens of thousands more crowns wherein the portion of the tension wires 318, 320 forming each crown has only been used once. This process can be repeated as many times as desirable and reduces damage to the stent wires caused by wear on forming members that occurs in other methods and apparatus for forming waves in a stent wire.

Figure 30:
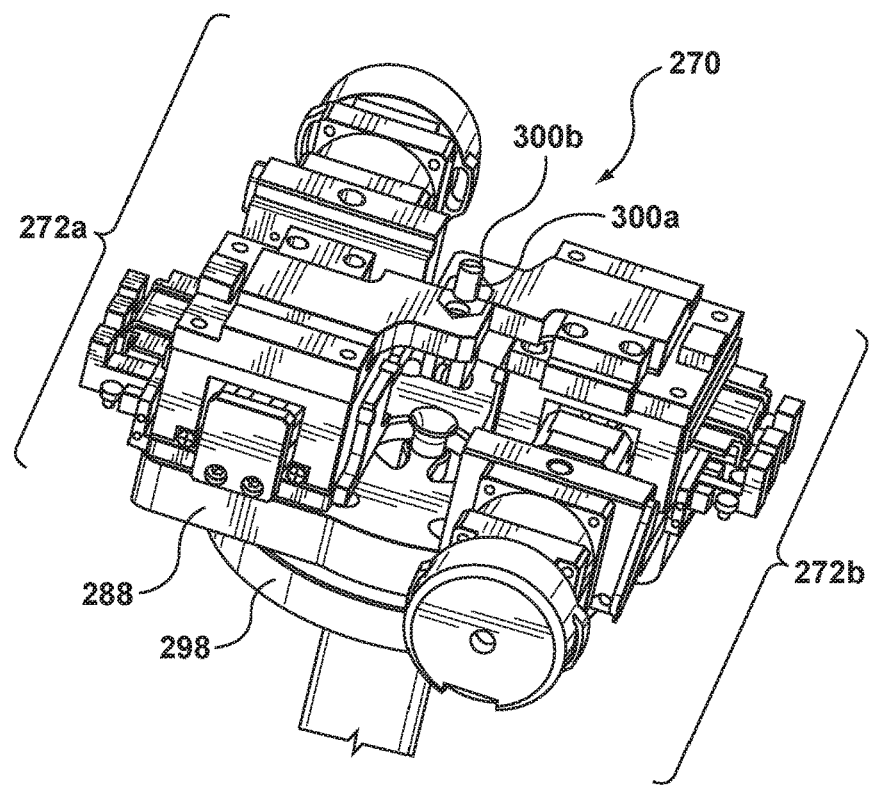
FIG. 30 is a perspective view of the rotation assembly of the apparatus of FIG. 24.

FIG. 30 shows a perspective view of rotation assembly 270. Rotation assembly 270 includes wire holders 300a, 300b coupled to stepper motors 272a, 272b to translate wire holders 300 and coupled to a rotary motor 290 (see FIG. 35, inner top 298 of rotary motor 290 is shown in FIG. 30) to rotate wire holders 300.

Figure 31:
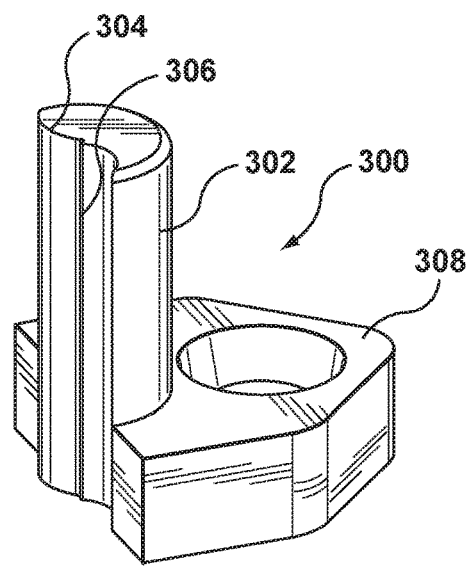
FIG. 31 is a perspective view of one of the wire holders of the rotation assembly of FIG. 30.

In particular, FIG. 30 shows wire holders 300a, 300b operatively connected to stepper motors 272a, 272b and rotary motor 290 (not shown in FIG. 30; inner top 298 of rotary motor 290 is shown in FIG. 30). Wire holders 300a, 300b are an embodiment of wire holders 118, 120 described above with respect to FIGS. 10-21. FIG. 31 shows a single wire holder 300. Wire holders 300a, 300b are mirror images such that description of wire holder 300 referring to FIG. 31 applies to both wire holders 300a, 300b. As shown in FIG. 31, each wire holder 300 includes a generally semi-cylindrical portion 302 with a curved parting surface 304 and a groove 306. The curved parting surface 304 of each wire holder defines where wire holders 300a, 300b separate from each other and come together towards each other. The groove 306 in each wire holder 300 is sized and configured to hold one of tension wires 318, 320 therein. Wire holders 300a, 300b together are generally cylindrical in shape and each has a base 308 to connect the respective wire holder 300 to the respective stepper motor 272.

Figure 32:
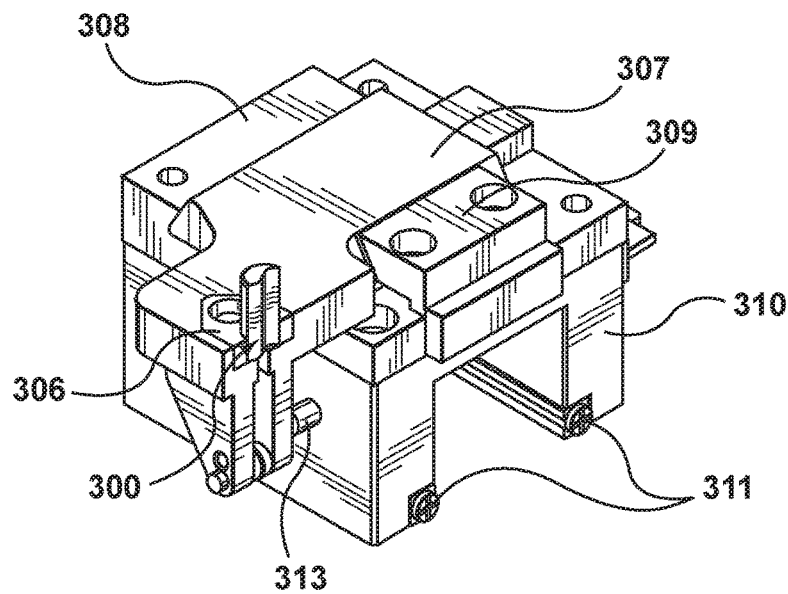
FIGS. 32 and 33 are perspective views of one of the carriage blocks and wire holder assemblies of the rotation assembly of FIG. 30.
Figure 33:
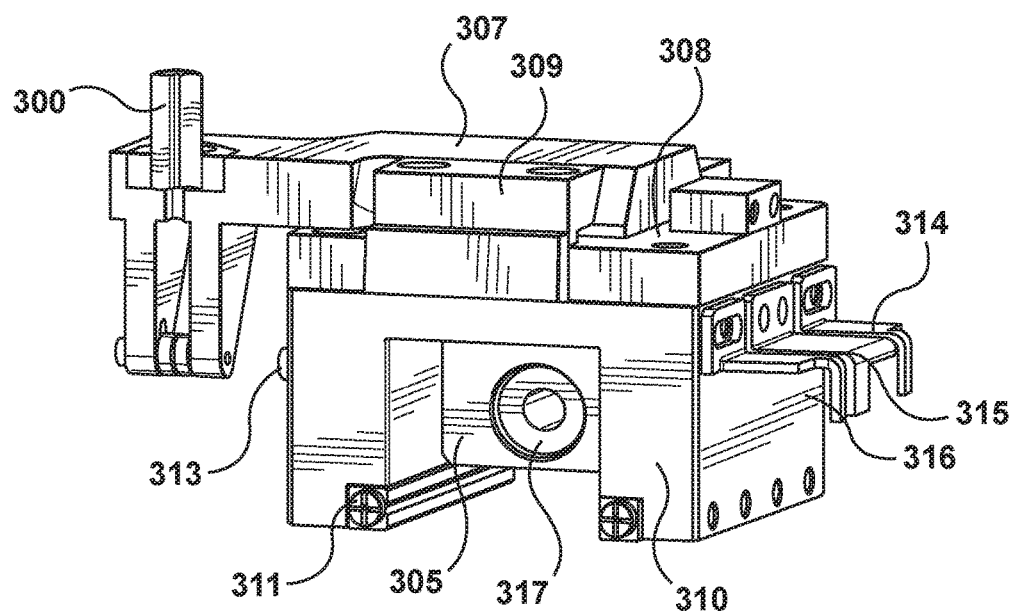
Figure 34:
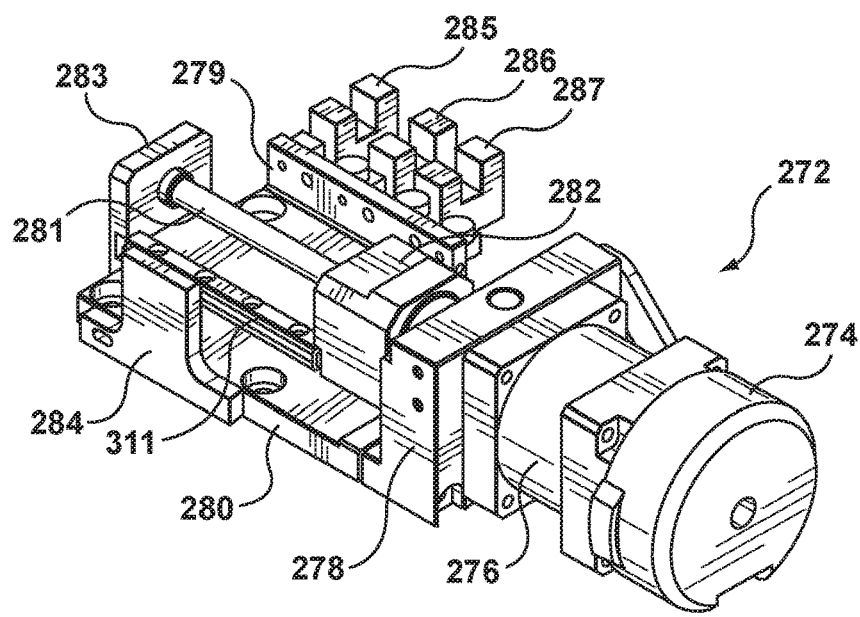
FIG. 34 is a perspective view of a portion of one of the stepping motors of the rotation assembly of FIG. 30.

Stepper motors 272a, 272b are shown in FIG. 30 and portions thereof are shown in FIGS. 32-34. As with wire holders 300, a stepper motor 272 and associated connectors to a respective wire holder will be described with respect to FIGS. 32-34. As is apparent, steppers motors 272a, 272b are the same except that they are mounted to carriage plate 298 in opposite directions.

As shown in FIGS. 32-33, each wire holder 300 is mounted to wire holder adjuster 307. Wire holder adjuster 307 is mounted to wire holder mount 308 by wire holder clamp 309. Wire holder mount 308 is attached to a carriage block 310, which moves with the movement of stepper motor 272, thereby moving the wire holder 300. Carriage plate 310 is part of stepper motor 272, described in detail below, and is coupled to a screw 281 (see FIG. 34) of stepper motor 272 by a screw nut 317 which is coupled to carriage plate 310 by a nut block 305. Carriage block 310 moves along cross roller rails 311. Home flag 315 and limit flags 314, 316 are coupled to carriage block 310 and coordinate with home sensor 286 and limit sensors 285, 287 (see FIG. 34) to provide feedback regarding the location of carriage plate 310, and hence the location of wire holder 300. Dowel pins 313 are also coupled to carriage block 310 (only one of two dowel pins is shown in the figures). Dowel pins 313 prevent carriage block 310 from moving beyond a certain point in each direction when a respective dowel pin 313 hits a limit stop 284 (see FIG. 34).

Stepper motor 272, with carriage block 310 removed, is shown in FIG. 34. It is apparent that stepper motor 272 described herein is exemplary and that other stepper motors or similar devices may be used to move wire holders 300a, 300b. Stepper motor 272 described herein may be, for example and not by way of limitation, an AM1-0401-3S motorized staged AM series motor available from Micro Motion Technology, LTD. A modular encoder 274 may be coupled to stepper motor 272. For example, and not by way of limitation, an R35i series modular encoder available from RENCO encoders, Inc. may be utilized. As shown in FIG. 34, stepper motor 272 further includes a stepping motor 276 mounted to a motor bracket 278, which is mounted to a base plate 280. Base plate 280 includes a support block 282 and end block 283 mounted thereon. Support block 280 and end block 283 support a screw 281 therebetween. Rotation of screw 281 causes carriage block 310 to translate by the connection through screw nut 317. Cross roller rails 311 are also mounted to base plate 280, although only one is shown in FIG. 34. A limit stop 284 is also mounted to base plate 280. With carriage block 310 coupled to screw 281; limit stop 284 is disposed between dowels 313 coupled to carriage block 310. Thus, dowels 313 and limit stop 284 limit the movement of carriage block 310 in each direction because limit stop 284 will hit one of the dowels 313, depending on which direction carriage block 310 is moving. Home sensor 286 and limit sensors 285, 287 are also coupled to base plate 280 via a sensor block 279. Sensors 285, 286, 287 are disposed such that flags 314, 315, 316 mounted on carriage block 310 trigger sensors 285, 286, 287 to provide feedback to a control unit regarding the location of carriage block 310.

Figure 35:
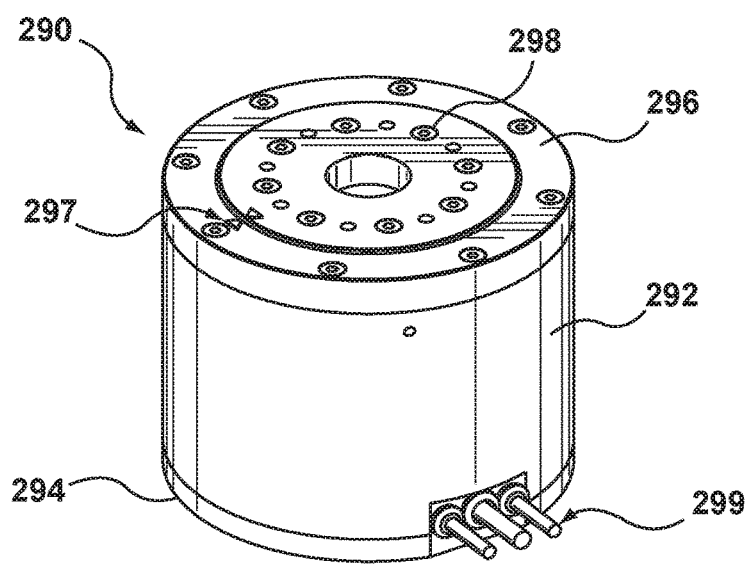
FIG. 35 is a perspective view of the rotary motor of the rotation assembly of FIG. 30.

As shown in FIG. 30, the stepper motors 272a, 272b and thus the wire holders 300a, 300b coupled thereto, are mounted on a carriage plate 288. Carriage plate 288 is attached to an inner top 298 of a rotary motor 290. As shown in FIG. 35, rotary motor includes a body 294, a base 292, an outer ring 296, and inner top 298. Rotary motor 290 rotates inner top 292 in a clockwise or counter-clockwise direction, thereby rotating carriage plate 288 and the items mounted thereon, in a clockwise or counter-clockwise direction. Consequently, rotary motor 290 rotates wire holders 300a, 300b in a clockwise or counter-clockwise direction. Outer ring 296 and inner top 292 may each include a home marker 297 indicating the home or neutral position of inner top 298. Rotary motor 290 also includes cables/bushings 299 as known to those skilled in the art. Rotary motor 290 may be any rotary motor that can rotate carriage plate 288 as desired. For example, and not by way of limitation, rotary motor 290 may be an ACD series coreless torque motor available from Motion Control Products LTD.

FIGS. 36-39 illustrate an embodiment of a feed assembly 240 to feed a stent wire into the forming area between tension wires 318, 320. Those of ordinary skill in the art will recognize that other feed assemblies may be utilized.

Figure 36:
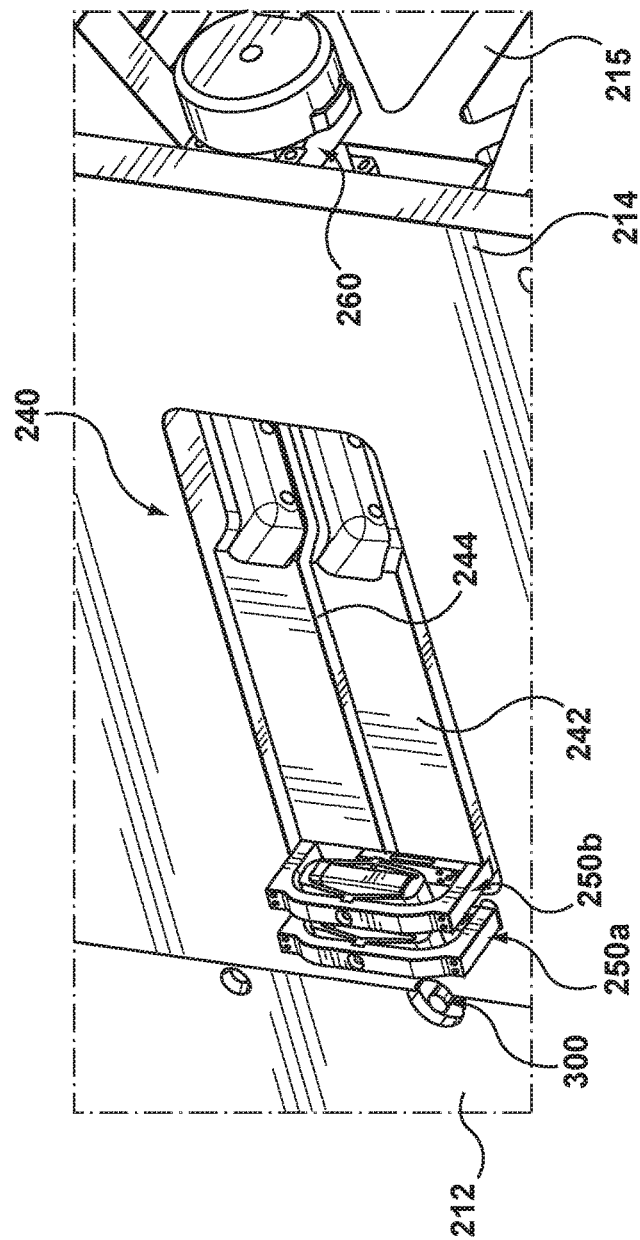
FIG. 36 is a perspective view of the feed assembly portion of the apparatus of FIG. 24.
Figure 37A:
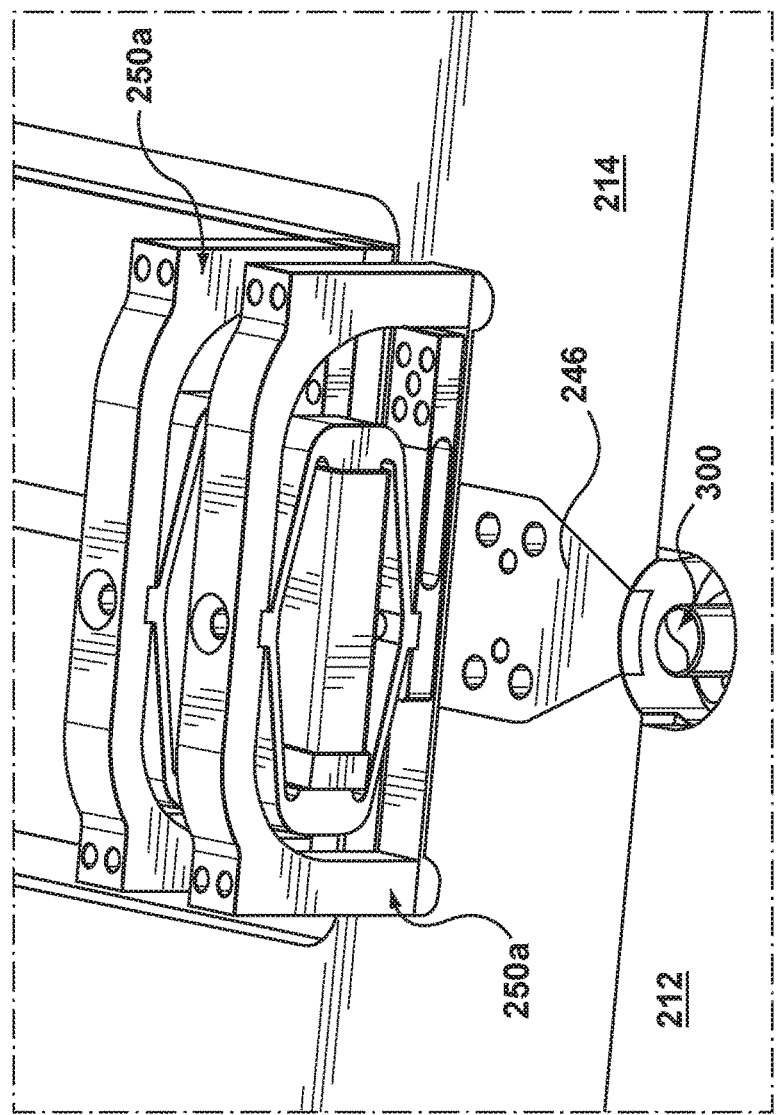

As illustrated in FIGS. 36, 37A, and 37B, feed assembly 240 includes a feed axis arm 242 including a groove 244. Feed assembly 240 further includes a first brake assembly 250a and a second brake assembly 250b, described in detail below. The stent wire is fed through openings in the brake assemblies 250a, 250b and over a lower wear plate 246, shown in FIG. 37A. Those of ordinary skill in the art will recognize that a separate wear plate is not necessary. FIG. 37B illustrates the same area of FIG. 37A except that an upper guide plate 248 is shown covering the general area of the lower wear plate 246. In operation, the stent wire is fed between lower wear plate 246 and upper guide plate 248 in order to guide the stent wire to the forming area at wire holders 300a, 300b.

Feed axis arm 242 is operatively coupled to a feed motor 260, as illustrated in FIG. 36. Feed motor 260 in this embodiment is the same as stepping motors 272 except that the carriage block of feed motor 260 is attached to feed axis arm 242 rather than to the wire holder mount 308. Feed motor 260 operates to translate feed axis arm back and forth in the longitudinal direction of groove 244. Although feed motor 260 is shown and described as being the same as stepping motors 272, those of ordinary skill in the art will recognize that feed motor can be any device that can move feed axis arm 242 in the longitudinal direction. Feed motor 260 may be, for example and not by way of limitation, an AM1-0401-35 motorized staged AM series motor available from Micro Motion Technology, LTD.

Brake assemblies 250a, 250b operate to hold or release the stent wire so as to feed the stent wire into the forming area. Front brake assembly 250a is mounted to the rear upper shelf 214 and is substantially fixed. In an embodiment, front brake assembly may shift slightly laterally such that the stent wire is aligned when the wire holders 300 shift to align the center of rotation with one of the tension wires 318, 320, as described above with respect to FIGS. 10-21. Rear brake assembly 250b is operatively coupled to feed axis arm 242 such that rear brake assembly 250b moves with feed axis arm 242.

Figure 38:
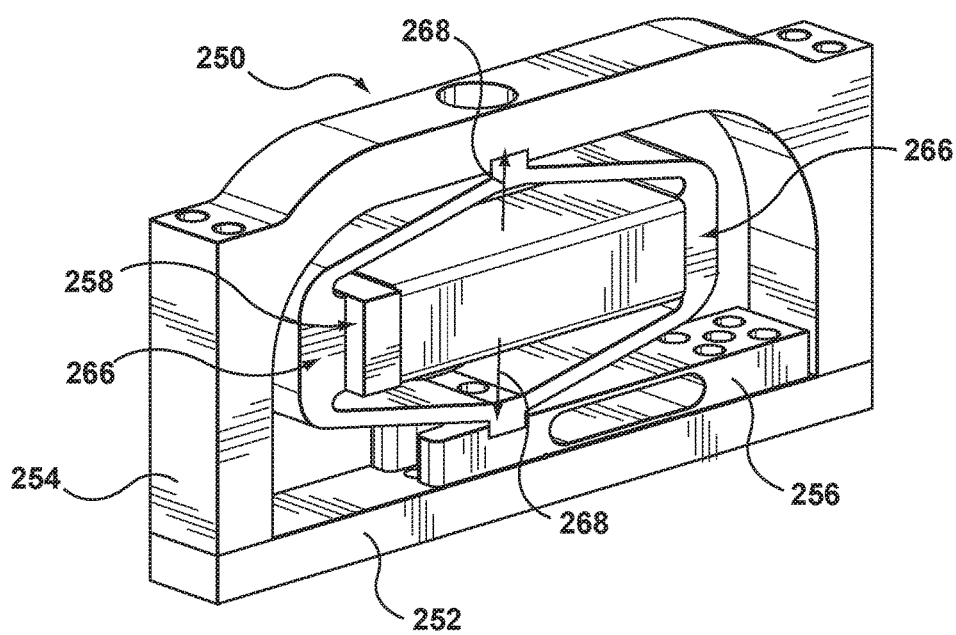
FIG. 38 is a perspective view of one of the brake assemblies of the feed assembly of FIG. 36.
Figure 39:
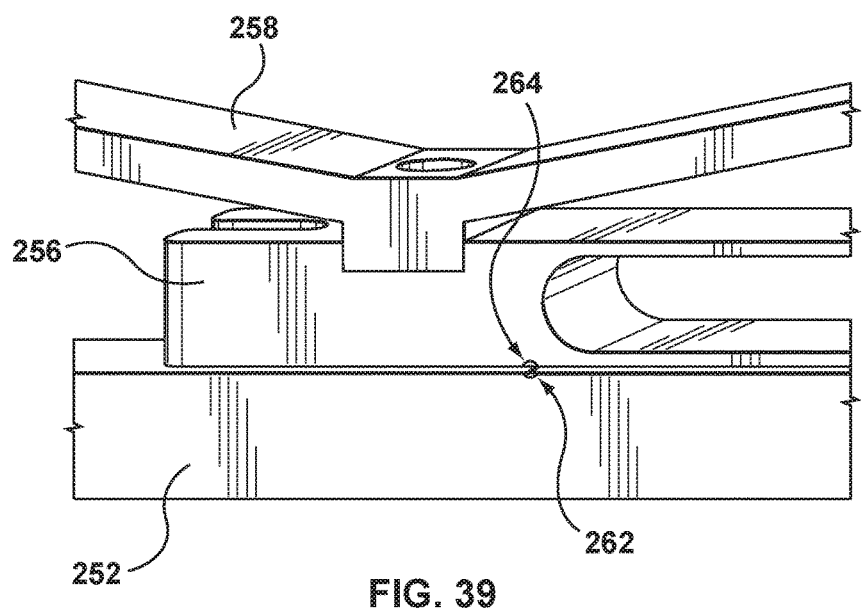
FIG. 39 is an enlarged view of a portion of the brake assembly of FIG. 38.
Figure 40:
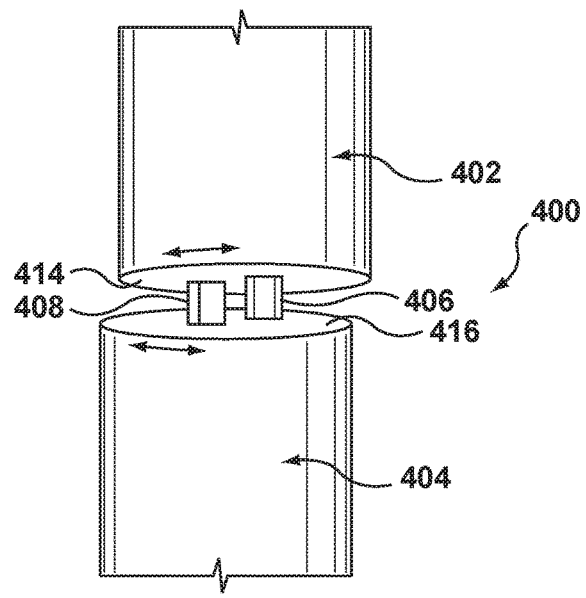
FIGS. 40-54 are schematic views of an embodiment of an apparatus and a method for forming a wave form for a stent from a wire.

Brake assemblies 250a, 250b in the present embodiment are identical and thus one brake assembly 250 is illustrated and described in FIGS. 38-39. Those of ordinary skill in the art will recognize that the description applies to both brake assemblies. Further, those of ordinary skill in the art will recognize that the brake assemblies 250a, 250b do not need to be the same and do not need to be as described herein. Other assemblies for feeding the stent wire into the forming area may also be used. Brake assembly 250 includes brake flexure base 252 for mounting the brake assembly to the upper rear shelf 214 or the feed axis arm 242. Brake assembly 250 further includes a brake bridge 254 coupled at each end thereof to the brake flexure base 252. A brake flexure top side 256 is disposed on a top portion of brake flexure base 252. A piezo actuator 258 is mounted between brake bridge 254 and brake flexure top side 256. As illustrated in FIG. 39, each of brake flexure base 252 and brake flexure top side 256 includes a respective groove 262, 264 in the mating surfaces thereof to form a hole through which the stent wire is fed.

Piezo actuator 258 may be any device that can apply pressure to brake flexure top side 256 such that a gripping pressure is applied to the sent wire disposed between brake flexure top side 256 and brake flexure base 252. In the embodiment shown, piezo actuator 258 is actuated to compress in the direction of arrows 266 such that the portions of piezo actuator 258 attached to brake bridge 254 and brake flexure top side 256 expand in the directions shown by arrows 268. This expansion provides a force against brake flexure top side 256 that compresses the hole formed by grooves 252, 254, thereby gripping a stent wire disposed in the hole. Piezo actuator 258 may be, for example and not by way of limitation, a piezo actuator in the Amplified Piezo Actuator Series available from Cedrat Technologies, such as model APA-60S.

In operation, when a length of the stent wire is to be fed into the forming area, second brake assembly 250b is actuated such that a gripping pressure is applied to the stent wire, while first brake assembly 250a remains un-actuated such that the stent wire may pass therethrough. While second brake assembly 250b is actuated, feed motor 260 is actuated to move feed axis arm 242 towards the feed area, thereby also moving second brake assembly 250b, and the stent wire captured therein, towards the feed area. This movement can also be described as moving the feed axis arm 242 and the second brake assembly 250b towards the first brake assembly 250a. The first brake assembly 250a is then actuated to grip the stent wire while the second brake assembly 250b is un-actuated to release the stent wire and the feed motor 260 moves feed axis arm 242 away from the feed area/first brake assembly 250a. Thus, during the first movement, a length of the stent wire is moved into the feed area while the second movement returns the feed axis arm 242 and second brake assembly 250a to a neutral position while the first brake assembly 250a holds the stent wire in place such that the stent wire is not retracted from the feed area. This process is repeated for each length of the stent wire fed into the forming area to bend the stent wire to form a wave of the waveform.

Figure 56:
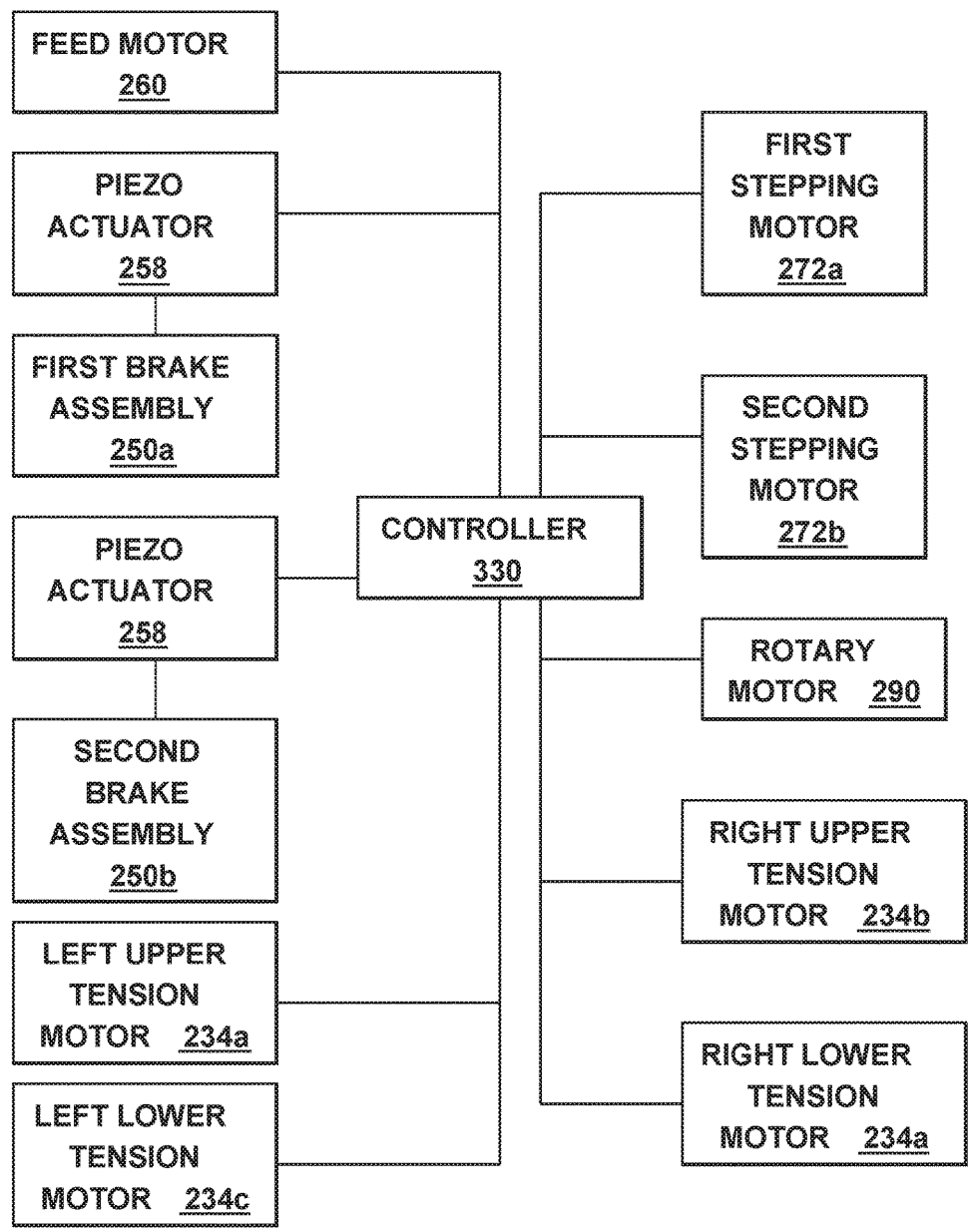
FIG. 56 is a schematic block diagram that illustrates communication between a controller and parts of the apparatus of FIGS. 23-39.

In operation, a controller 330, shown schematically in FIG. 56, communicates with the first and second stepping motors 272a, 272b, the rotary motor 290, the feed motor 260, the piezo actuators 258 of the first and second brake assemblies 250a, 250b, and the left upper, right upper, left lower, and right upper tension motors 234a, 234b, 234c, 234d. Thus, the piezo actuators 258 and feed motor 260 are controlled to feed the stent wire into the wire forming area between the tension wires 318, 320, the first and second stepping motors 272a, 272b, are controlled to translate wire holders 300a, 300b such as to bring the wire holders together, separate them, or shift them such that the axis of rotation is aligned with one of the tension wires 318, 320, the rotary motor 290 is controlled to rotate wire holders 300a, 300b and thus rotate wires 318, 320, and the tension motors 234 are controlled to keep tension wires 318, 320 in tension and to shift tension wires 318, 320 longitudinally after each bend of the stent wire in order to minimize wear. Once the desired wave form has been communicated to the controller 330, and the controller 330 is able to access a computer readable medium that contains a method for forming the desired wave form, as described herein, the controller 330 may signal the motors and actuators described above so the apparatus 200 forms the desired wave form.

FIGS. 40-55 illustrate schematically an apparatus 400 for forming a waveform in a stent wire 412 and a method for forming a waveform in a stent wire in accordance with another embodiment hereof. Rather than using wires in tension to bend the stent wire, apparatus 400 uses forming members, as will be described in more detail below.

Apparatus 400 includes an upper or first drum or cylinder 402 and a lower or second drum or cylinder 404. First drum 402 includes a first surface 414 and second drum 404 includes a second surface 416. First surface 414 and second surface 416 face each other. First drum 402 further includes a first bending or forming member 406 disposed on first surface 414. Second drum 404 includes a second bending or forming member 408 disposed on second surface 416. First drum 402 and second drum 404 may move independently of each other and each may rotate in either direction and may translate in four directions, in an x-y plane, as indicated by the arrows in FIG. 40. First and second drums 402, 404 may be rotated, about a local z-axis, and translated by mechanisms known to those skilled in the art. For example, and not by way of limitation, the mechanisms described above for rotation and translation may be utilized. Further, although drums 402, 404 are shown as generally cylindrical drums, those skilled in the art would recognize that they can be different shapes provided that they can perform the functions described below.

Figure 41:
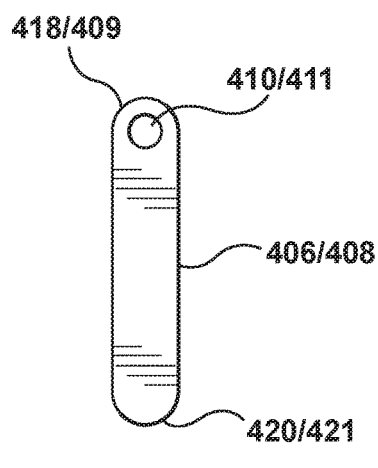
Figure 42:
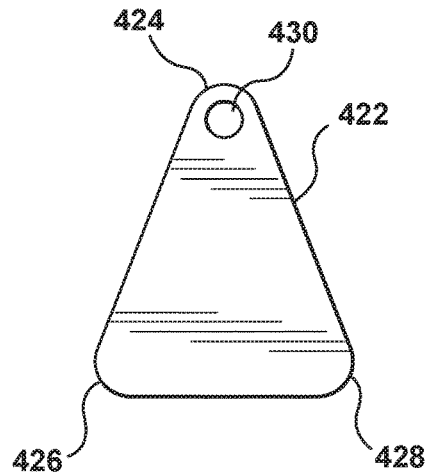

Forming members 406, 408 may be elongated members with rounded ends. For example, and not by way of limitation, forming members 406, 408 may be generally rectangular in shape with rounded ends 418, 419 and 420, 421 instead of straight ends, as illustrated in FIG. 41. Each forming member 406, 408 is mounted to the respective surface 414, 416 of the respective drum 402, 404 such that a center of rotation 410, 411 of rounded end 418, 419 of the forming member 406, 408 is aligned with the center of rotation of the respective drum 402, 404. The forming members may be different shapes. For example, and not by way of limitation, FIG. 42 illustrates schematically an embodiment of a forming member 422. Forming member 422 is generally triangular in shape with rounded edges 424, 426, 428 at the apices of the triangle. FIG. 42 illustrates a plan view of forming member 422. Forming member 422 also includes a depth or thickness, as is apparent from FIG. 40. If forming members such as forming member 422 are used, forming members 422 would be mounted to drums 402, 404 such that a center of rotation 430 of a rounded apex 424 of forming member 424 is aligned with a center of rotation of the drum 402, 404 to which forming member 422 is mounted. Forming members 406, 408, or 422 may be made of any material suitable to withstand the wear of bending the stent wire, as described below, and sufficiently smooth so as not to create unwanted surface marks or deformations in the stent wire. For example, and not by way of limitation, the forming members may be made of hardened tool steel (high speed steel), tungsten alloys or tungsten-carbide, cobalt or cobalt-steel alloys. The surface of the forming member 406,408,422 may also be coated to reduce wear. For example, and not by way of limitation, the forming members may be coated with black oxide, titanium nitride (TiN), titanium aluminum nitride (TiAlN), titanium carbon nitride (TiCN), aluminum chromium silicon nitride (AlCrSiN), titanium silicon nitride (TiSiN), or diamond. The operation of apparatus 400 is described below and illustrated with forming members 406, 408. However, it would be understood by those skilled in the art that other forming members, such as forming member 422 or others may be utilized.

Figure 43:
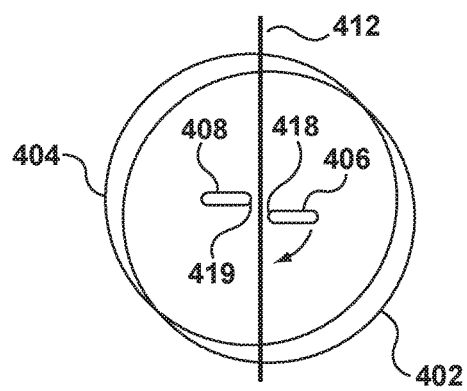

FIGS. 43-54 illustrate schematically an embodiment of operation of apparatus 400 in an embodiment of a method of forming a waveform in a stent wire 412. FIG. 43 shows a length of stent wire 412 already fed between forming members 406, 408 and between first surface 414 of first drum 402 and second surface 416 of second drum 404. Stent wire 412 may be fed by devices and methods described above for feeding a stent wire, other devices and methods known to those skilled in the art, or using the forming members 406, 408 and movement of the drums 402, 404, as will be described below.

Figure 44:
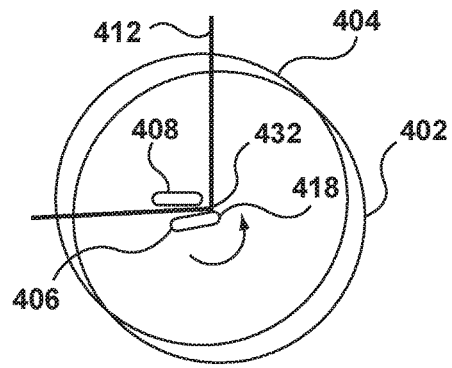

Stent wire 412 is disposed between forming members 406, 408 with forming members disposed generally perpendicular to stent wire 412. Further, forming members 406, 408 are offset from each other along the direction of stent wire 412, as shown schematically in FIG. 43. Forming members 406, 408 are disposed with respective ends 418, 419 with centers of rotation 410, 411 aligned with the centers of rotation of drums 402, 404 adjacent stent wire 412, as shown in FIG. 43. As indicated by the arrow in FIG. 43, first drum 402 is rotated clockwise approximately 180 degrees, resulting in the first forming member 406 rotating around end 418 such that first forming member is generally parallel to second forming member 408, as shown in FIG. 44. As first drum 402 is rotated, stent wire 412 is bent by first and second forming members 406, 408, as shown schematically in FIG. 44, to create a first crown 432 in stent wire 412.

Figure 45:
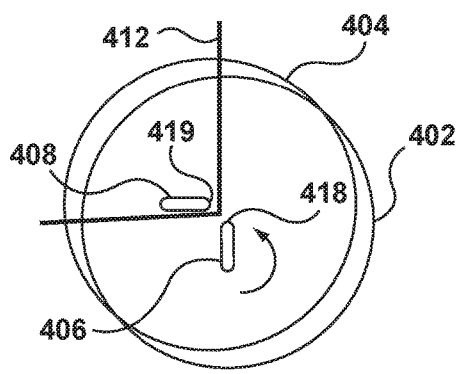

Next, first drum 402 is rotated counter-clockwise approximately 90 degrees as indicated by the arrow in FIG. 44, resulting in first forming member 406 being generally perpendicular to second forming member 408, as shown in FIG. 45. First drum 402 continues its clockwise rotation another approximately 180 degrees, as indicated by the arrow in FIG. 45, resulting in the first forming member 406 rotating around end 418, as shown schematically in FIG. 46. Next, second drum 404 is translated in a direction generally parallel to the feed direction of stent wire 412, as indicated by the arrow in FIG. 46, resulting in stent wire 412 being pushed by first forming member 406, as shown in FIG. 47. This movement results in a length of stent wire 412 disposed between first crown 432 and first forming member 406, as shown in FIG. 47. This movement also results in second drum 404 being offset from first drum 402 such that second forming member 408 is offset from first forming member 406, as also shown in FIG. 47.

Figure 46:
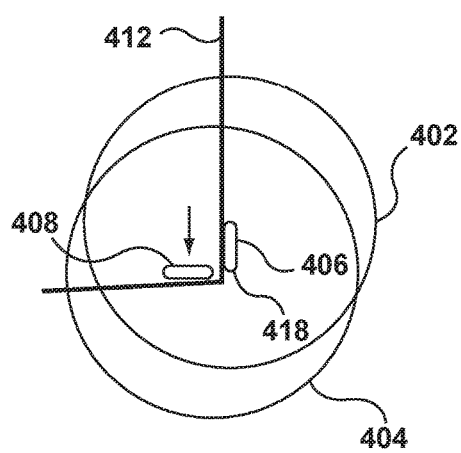
Figure 47:
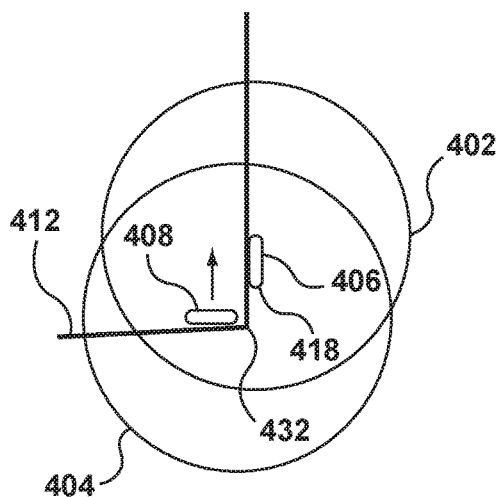
Figure 48:
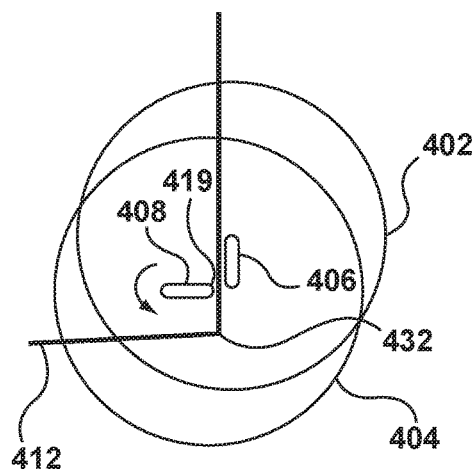

Next, as indicated by the arrow in FIG. 47, second drum 404 and corresponding second forming member 408 are translated in a direction opposite the feed direction of stent wire 412 back to the position shown in FIG. 46, as shown in FIG. 48. This movement results in the first and second forming members 406, 408 being located in positions to form a second crown 434. Next, as indicated by the arrow in FIG. 48, second drum 404 is rotated counter-clockwise such that corresponding second forming member 408 rotates counter-clockwise, as indicated by the arrow in FIG. 48. The rotation of second forming member 408 causes the portion of stent wire 412 disposed between second forming member 408 and first forming member 406 to bend to form a first portion of second crown 434, as shown in FIG. 49.

Figure 49:
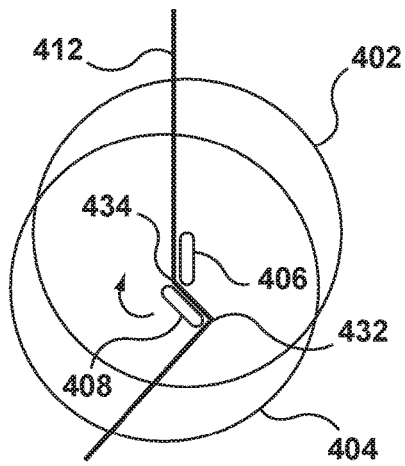
Figure 50:
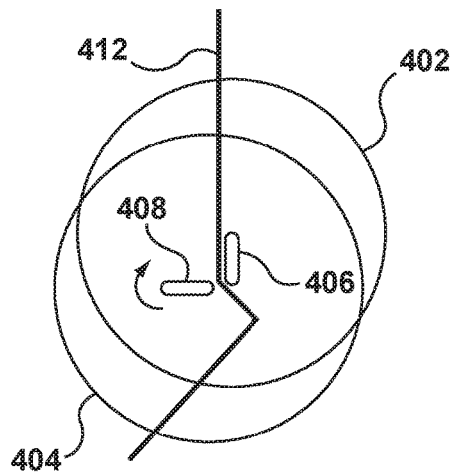
Figure 51:
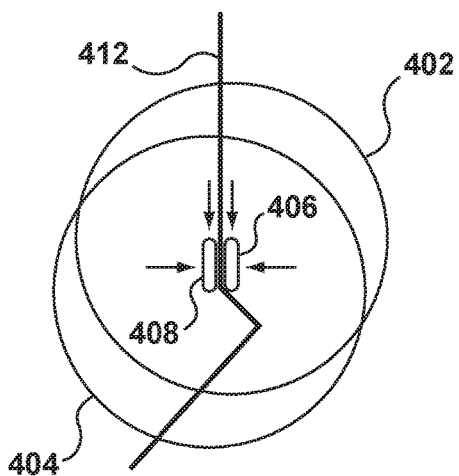

Next, second drum 404 and corresponding second forming member 408 are rotated clockwise, as indicated by the arrows in FIGS. 49 and 50. This rotation results in first and second forming members 406, 408 being parallel to each other and parallel to the feeding direction of stent wire 412, as shown in FIG. 51. Next, first and second drums 402, 404 are translated towards each other such that first and second forming members 406, 404 move towards each other and towards stent wire 412, which is disposed between the first and second forming members 406, 408, as indicated by the arrows in FIG. 51. The first and second forming members 406, 408 apply sufficient pressure on stent wire 412 such that stent wire 412 moves with first and second forming members 406, 408. In particular, first and second drums 404, 404 are then translated together in the feed direction of stent wire 412, as also indicated by the arrows if FIG. 51. This movement results in a length of stent wire 412 being fed from the stent wire supply (not shown).

Figure 52:
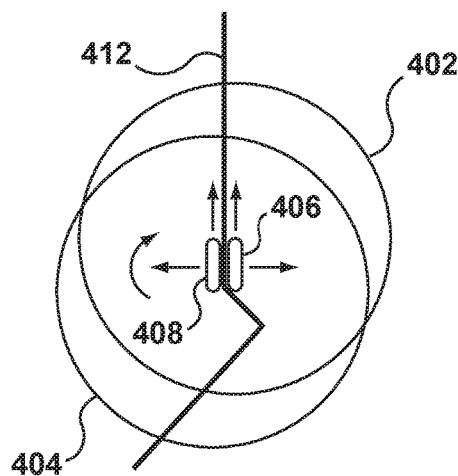
Figure 53:
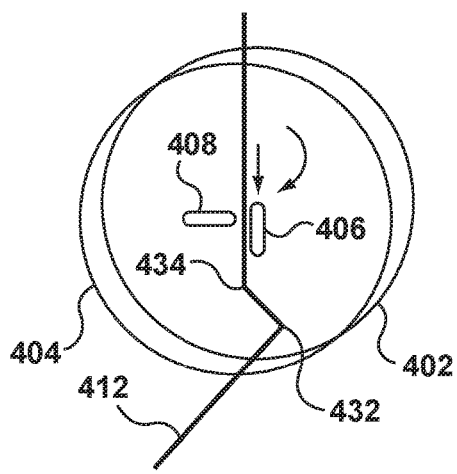
Figure 54:
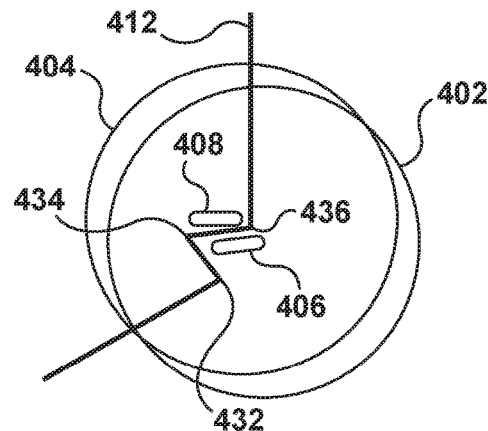

Next, first and second drums 402, 404 are translated away from each other such that first and second forming members 406, 408 move apart from each other to relieve the pressure applied to stent wire 412, as indicated by the arrows in FIG. 52. First and second drums 402, 404 are also translated in a direction opposite the feed direction of stent wire 412, as also indicated by the arrows in FIG. 52. This movement of first and second drums results in a length of stent wire 412 being disposed between the first portion of second crown 434 and first and second forming members 406, 408, as shown in FIG. 53. Second drum 404 is also rotated in a clockwise direction, as indicated by the rotational arrow in FIG. 53, resulting in second forming member 408 being generally perpendicular to first forming member 406, as shown in FIG. 53.

Next, first drum 402 is translated in the feed direction of stent wire 412, as indicated by the arrow in FIG. 53, thereby translating first forming member 406 in the feed direction. First drum 402 is then rotated clockwise as indicated by the rotational arrow in FIG. 53, resulting in first forming member 406 rotating to bend stent wire 412 disposed between first forming member 406 and second forming member 408 to form the second portion of second crown 434 to complete a wave of the waveform and to form a third crown 436, which is the first crown of the next wave of the waveform, as illustrated schematically in FIG. 54.

The above-described steps may then be repeated as many times as desired to complete the desired waveform. The size and shape of each individual wave may be controlled by controlling the length of stent wire 412 fed from between first and second forming members 406, 408 and the amount of rotation of first and second drums 402, 404. Thus, a waveform with varying wave lengths, amplitudes, and degree of bend in the crowns may be created from a single stent wire. As noted above, in the embodiment described in FIGS. 40-54, the stent wire 412 may be fed by movement of first and second drums 402, 404 and corresponding first and second forming members 406, 408. In such an embodiment, the supply for stent wire 412 may simply be a spool of stent wire 412 or other similar supply. Alternatively, an active feed system may be provided for stent wire 412, such as the feed assembly 240 described in other embodiments herein or known to those skilled in the art, and the steps described above for feeding stent wire 412 using first and second forming members 406, 408 may be eliminated.

Figure 55:
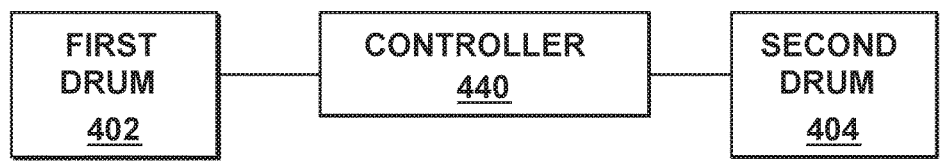
FIG. 55 is a schematic block diagram that illustrates communication between a controller and parts of the apparatus of FIGS. 40-54.

FIG. 55 schematically illustrates communication between a controller 440 and other parts of the apparatus 400 that are illustrated in FIGS. 40-54. As illustrated, the controller 440 is configured to communicate with the first drum 402 and second drum 404. As discussed above, first and second drums 402, 404 are configured to rotate and translate. Thus, the devices used to rotate and translate first and second drums 402, 404, such as linear slides/actuators, stepping motors, and rotary motors (not shown), communicate with controller 440. Once the desired wave form has been communicated to the controller 440, and the controller 440 is able to access a computer readable medium that contains a method for forming the desired wave form, as described herein, the controller 440 may signal the first drum 402 and second drum 404 so the apparatus 400 forms the desired wave form.

While several exemplary embodiments have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A method for forming a wave form for a stent from a stent wire, the method comprising:
   maintaining a first tension wire and a second tension wire in tension;
   moving a first wire holder with the first tension wire and a second wire holder with the second tension wire apart from each other;
   feeding the stent wire such that a first portion of the stent wire is disposed between the first tension wire and the second tension wire, wherein the stent wire is substantially orthogonal to the first and second tension wires;
   moving the first wire holder and the second wire holder towards each other;
   rotating the first and second wire holders in a first direction about a rotation axis substantially parallel to the first and second tension wires to bend the first portion of the stent wire in a first direction;
   moving the first wire holder and the second wire holder apart from each other;
   feeding the stent wire such that a second portion of the stent wire is disposed between the first and second tension wires;
   moving the first wire holder and the second wire holder towards each other; and
   rotating the first and second wire holders in a second direction substantially opposite the first direction about the rotation axis to bend the second portion of the stent wire in a second direction substantially opposite the first direction.

2. The method of claim 1, further comprising:
   prior to rotating the first and second wire holders in the first direction, translating the first wire holder such that the first tension wire is substantially aligned with the rotation axis.

3. The method of claim 2, further comprising:
   prior to rotating the first and second wire holders in the second direction, translating the second wire holder such that the second tension wire is substantially aligned with the rotation axis.

4. The method of claim 1, further comprising: moving the first and second tension wires longitudinally after bending the stent wire such that a different portion of each of the first and second tension wires is disposed adjacent the stent wire.

5. The method of claim 1, wherein prior to rotating the first and second wire holders in the first direction, the first and second tension wires are abutting the stent wire.

6. The method of claim 5, wherein after the first and second wire holders are rotated in the first direction, the first and second wire holders are separated such that there is a gap between the stent wire and each of the first and second tension wires.

7. The method of claim 1, further comprising:
   after rotating the first and second wire holders in the first direction and prior to rotating the first and second wire holders in the second direction, rotating the first and second wire holders to a neutral position.

8. The method of claim 1, further comprising:
   controlling the length of stent wire fed prior to each bending step and controlling the amount of rotation of the stent wires for each bending step.

9. The method of claim 1, wherein maintaining the first and second tension wires in tension comprises a tension motor coupled to at least one end of each of the first and second tension wires.

10. The method of claim 9, wherein maintaining the first and second tension wires in tension comprises a first tension motor coupled to a first end of the first tension wire, a second tension motor coupled to a second end of the first tension wire, a third tension motor coupled to a first end of the second tension wire, and a fourth tension motor coupled to a second end of the second tension wire, wherein the first and second tension motors pull the first and second ends of the first tension wire in opposite directions, and wherein the third and fourth tension motors pull the first and second ends of the second tension wire in opposite directions.

11. The method of claim 10, wherein:
the first end of the first tension wire is coupled to a first pulley which is coupled to the first tension motor;
the second end of the first tension wire is coupled to a second pulley which is coupled to the second tension motor, wherein the first and second tension motors rotate the first and second pulleys to pull the first and second ends of the first tension wire in opposite directions;
the first end of the second tension wire is coupled to a third pulley which is coupled to the third tension motor; and
the second end of the second tension wire is coupled to a fourth pulley which is coupled to the fourth tension motor, wherein the third and fourth tension motors rotate the third and fourth pulleys to pull the first and second ends of the second tension wire in opposite directions.

12. The method of claim 1, wherein maintaining the first and second tension wires in tension comprises at least one weight coupled to at least one end of each of the first and second tension wires.

13. A method for forming a wave form for a stent from a stent wire, the method comprising:
moving a first wire holder with a first tension wire and a second wire holder with a second tension wire apart from each other;
feeding the stent wire such that a first portion of the stent wire is disposed between the first tension wire and the second tension wire, wherein the stent wire is substantially orthogonal to the first and second tension wires;
moving the first wire holder and the second wire holder towards each other;
translating the first wire holder such that the first tension wire is substantially aligned with a rotation axis;
rotating the first and second wire holders in a first direction about the rotation axis substantially parallel to the first and second tension wires to bend the first portion of the stent wire in a first direction;
moving the first wire holder and the second wire holder apart from each other;
feeding the stent wire such that a second portion of the stent wire is disposed between the tension wires;
moving the first wire holder and the second wire holder towards each other;
rotating the first and second wire holders in a second direction substantially opposite the first direction about the rotation axis to bend the second portion of the stent wire in a second direction substantially opposite the first direction; and
prior to rotating the first and second wire holders in the second direction, translating the second wire holder such that the second tension wire is substantially aligned with the rotation axis.

14. A method for forming a wave form for a stent from a stent wire, the method comprising:
maintaining a first tension wire and a second tension wire in tension;
feeding the stent wire such that a first portion of the stent wire is disposed between the first tension wire and the second tension wire, wherein the stent wire is substantially orthogonal to the first and second tension wires;
rotating the first and second tension wires in a first direction about a rotation axis substantially parallel to the first and second tension wires to bend the first portion of the stent wire in a first direction;
feeding the stent wire such that a second portion of the stent wire is disposed between the first and second tension wires; and
rotating the first and second tension wires in a second direction substantially opposite the first direction about the rotation axis to bend the second portion of the stent wire in a second direction substantially opposite the first direction.

15. The method of to claim 14, further comprising: prior to rotating the first and second tension wires in the first direction, translating the first tension wire such that the first tension wire is substantially aligned with the rotation axis.

16. The method of claim 15, further comprising: prior to rotating the first and second tension wires in the second direction, translating the second tension wire such that the second tension wire is substantially aligned with the rotation axis.

17. The method of claim 14, further comprising: moving the first and second tension wires longitudinally after bending the stent wire such that a different portion of each of the first and second tension wires is disposed adjacent the stent wire.

18. The method of claim 14, wherein prior to rotating the first and second tension wires in the first direction, the first and second tension wires are abutting the stent wire.

19. The method of claim 18, wherein after the first and second tension wires are rotated in the first direction, the first and second tension wires are separated such that there is a gap between the stent wire and each of the first and second tension wires.

20. The method of claim 14, further comprising: after rotating the first and second tension wires in the first direction and prior to rotating the first and second wires in the second direction, rotating the first and second tension wires to a neutral position.

* * * * *